(12) United States Patent
Revel et al.

(10) Patent No.: US 9,404,087 B2
(45) Date of Patent: Aug. 2, 2016

(54) INSULIN PRODUCING CELLS DERIVED FROM PLURIPOTENT STEM CELLS

(75) Inventors: Michel Revel, Rehovot (IL); Judith Chebath, Rehovot (IL); Guy Slutsky, Holon (IL); Alon Levy, Ramat-HaSharon (IL); Michal Izrael, Rehovot (IL); Arik Hasson, Kiryat-Ono (IL); Kfir Molakandov, Yahud (IL); Rosalia Kaufman, Rehovot (IL)

(73) Assignee: Kadimastem Ltd., Nes-Ziona (IL)

( * ) Notice: Subject to any disclaimer, the term of this patent is extended or adjusted under 35 U.S.C. 154(b) by 112 days.

(21) Appl. No.: 13/989,805

(22) PCT Filed: Dec. 15, 2011

(86) PCT No.: PCT/IL2011/050068
§ 371 (c)(1),
(2), (4) Date: May 27, 2013

(87) PCT Pub. No.: WO2012/081029
PCT Pub. Date: Jun. 21, 2012

(65) Prior Publication Data
US 2013/0273013 A1 Oct. 17, 2013

Related U.S. Application Data

(60) Provisional application No. 61/423,171, filed on Dec. 15, 2010.

(51) Int. Cl.
*C12N 5/00* (2006.01)
*C12N 5/071* (2010.01)
*C12N 5/02* (2006.01)

(52) U.S. Cl.
CPC ............ *C12N 5/0676* (2013.01); *C12N 5/0677* (2013.01); *C12N 2500/38* (2013.01); *C12N 2500/44* (2013.01); *C12N 2501/01* (2013.01); *C12N 2501/119* (2013.01); *C12N 2501/155* (2013.01); *C12N 2501/16* (2013.01); *C12N 2501/335* (2013.01); *C12N 2501/385* (2013.01); *C12N 2501/415* (2013.01); *C12N 2501/58* (2013.01); *C12N 2501/60* (2013.01); *C12N 2506/02* (2013.01); *C12N 2510/00* (2013.01); *C12N 2533/54* (2013.01); *C12N 2533/74* (2013.01)

(58) Field of Classification Search
CPC ............ C12N 5/0676; C12N 2506/02; C12N 5/0678; C12N 5/0607; C12N 2500/84; C12N 2501/119; C12N 5/0606; C12N 5/0689
See application file for complete search history.

(56) References Cited

U.S. PATENT DOCUMENTS 7,695,965 B2 * 4/2010 Martinson et al. ............ 435/377
2002/0019046 A1 2/2002 Carpenter et al.
2006/0194321 A1 * 8/2006 Colman et al. ................. 435/377
2007/0259421 A1 * 11/2007 D'Amour et al. ............. 435/366
2007/0259423 A1 * 11/2007 Odorico et al. ................ 435/366
2009/0093055 A1 * 4/2009 Fisk et al. ...................... 435/366
2009/0280096 A1 * 11/2009 Kubo et al. ................... 424/93.7

OTHER PUBLICATIONS

Chertow et al. Cellular Mechanisms of Insulin Release. Effects of Retinoids on Rat Islet Cell-to-Cell Adhesion, Reaggregation, and Insulin Release. Diabetes, 1983, 32:568-574.*
Kim et al. Differentiation of Mouse Embryonic Stem Cells into Endoderm without Embryoid Body Formation. PLOS One, 2010. 5(11):e14146, 1-8.*
Kuo et al. Formation of Pseudoislets from Human Pancreatic Cultures. Pancreas, 1992. 7(3) 320-325.*
International Search Report mailed on May 18, 2012 for PCT application No. PCT/IL2011/050068.
Bernardo et al., Biphasic Induction of Pdx1 in Mouse and Human Embryonic Stem Cells Can Mimic Development of Pancreatic β-Cells, Stem Cells, vol. 27, pp. 341-351, 2009.
D'Amour, Production of pancreatic hormone-expressing endocrine cells from human embryonic stem cells, Nature Biotechnology, vol. 24 No. 11, pp. 1392-1401, Nov. 2006.
Eshpeter et al., In vivo characterization of transplanted human embryonic stem cell-derived pancreatic endocrine islet cells, Cell Proliferation, vol. 41, pp. 843-858, 2008.
Ferber et al., Pancreatic and duodenal homeobox gene 1 induces expression of insulin genes in liver and ameliorates streptozotocin-induced hyperglycemia, Nature Medicine, vol. 6, No. 5, pp. 568-572, May 2000.
Jonsson et al., Insulin-promoter-factor 1 is required for pancreas development in mice, Nature, vol. 371, pp. 606-609, Oct. 13, 1994.
Kojima et al., Combined Expression of Pancreatic Duodenal Homeobox 1 and Islet Factor 1 Induces Immature Enterocytes to Produce Insulin, Diabetes, vol. 51, pp. 1398-1408, May 2002.
Sulzbacher et al., Activin A-Induced Differentiation of Embryonic Stem Cells into Endoderm and Pancreatic Progenitors—The Influence of Differentiation Factors and Culture Conditions, Stem Cell Rev, vol. 5, pp. 159-173, 2009.
Zalzman et al., Reversal of hyperglycemia in mice by using human expandable insulin-producing cells differentiated from fetal liver progenitor cells, PNAS, vol. 100, No. 12, pp. 7253-7258, Jun. 10, 2003.

* cited by examiner

*Primary Examiner* — Maria Leavitt
*Assistant Examiner* — Kimberly A Aron
(74) *Attorney, Agent, or Firm* — Pearl Cohen Zedek Latzer Baratz LLP

(57) ABSTRACT

A method of generating islet cells from pluripotent stem cells is disclosed. The method comprises: (a) culturing the pluripotent stem cells in a differentiation medium so as to differentiate the pluripotent stem cells into endoderm cells; and (b) culturing the endoderm cells in a medium comprising at least one growth factor, a cAMP inducer and retinoic acid (RA), said at least one growth factor being selected from the group consisting of FGF10, bFGF and FGF7 so as to generate further differentiated cells; and (c) culturing the further differentiated cells in a medium comprising a maturation factor selected from the group consisting of nicotinamide, GLP-1 and exendin 4, thereby generating islet cells from pluripotent stem cells. Further methods of generating islet cells are also disclosed, isolated cell populations comprising same and uses thereof.

19 Claims, 27 Drawing Sheets

FIGs. 1A-F
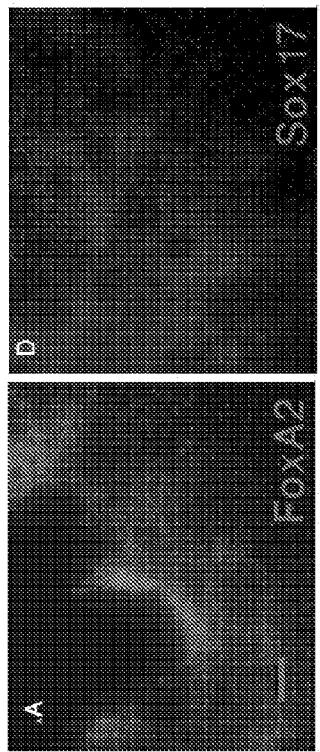
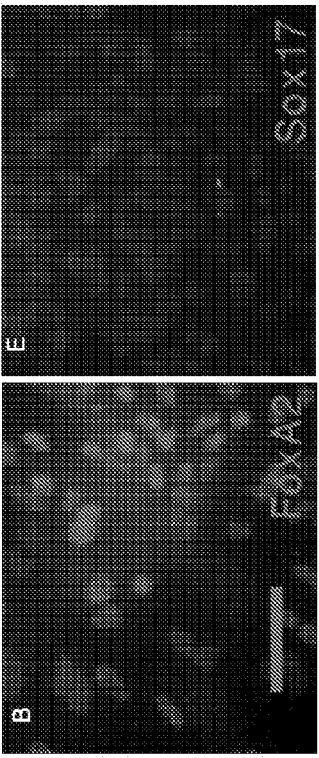
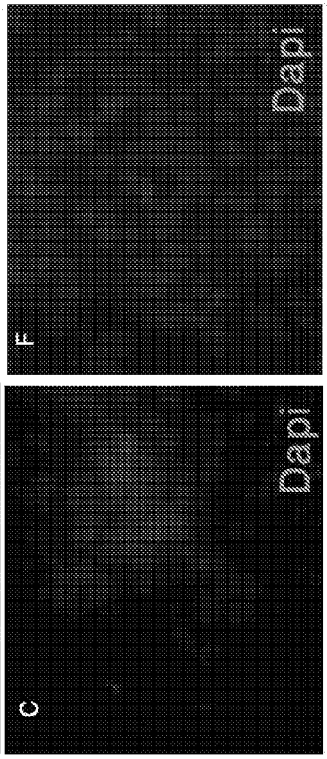
FIG. 1A  FIG. 1B  FIG. 1C  FIG. 1D  FIG. 1E  FIG. 1F

FIGs. 3A-D
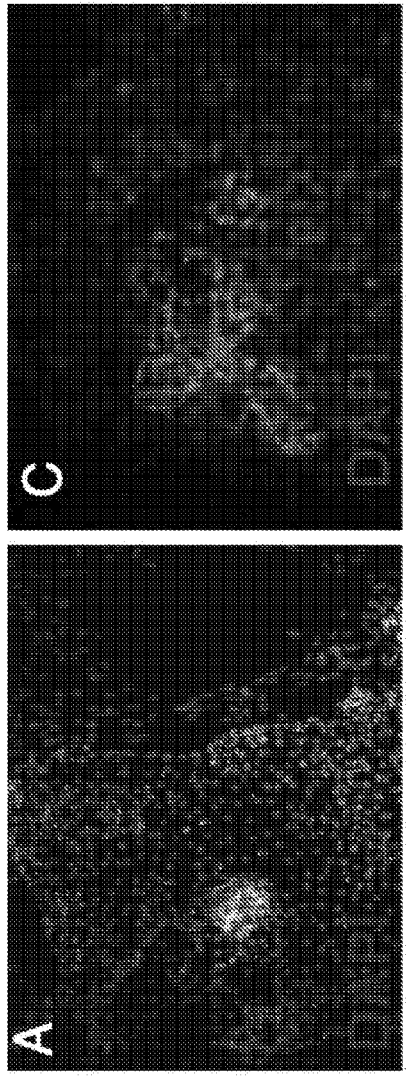
FIG. 3A
FIG. 3B
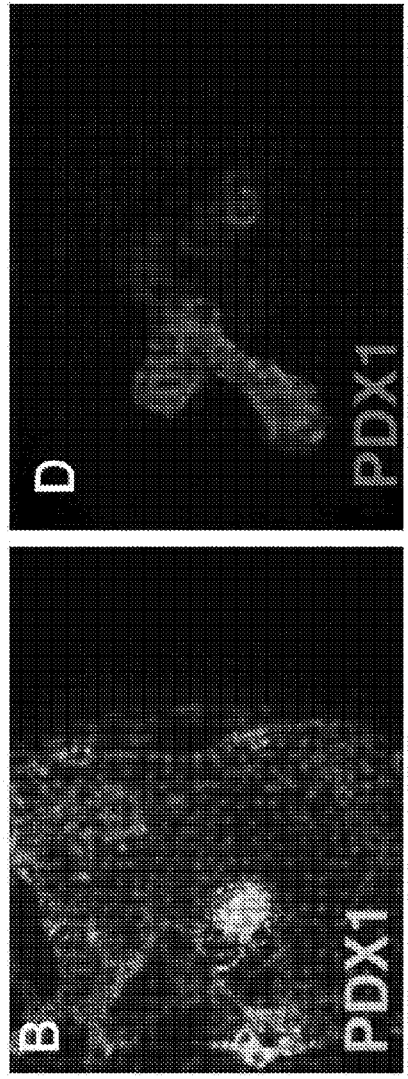
FIG. 3C
FIG. 3D

FIGs. 4A-C

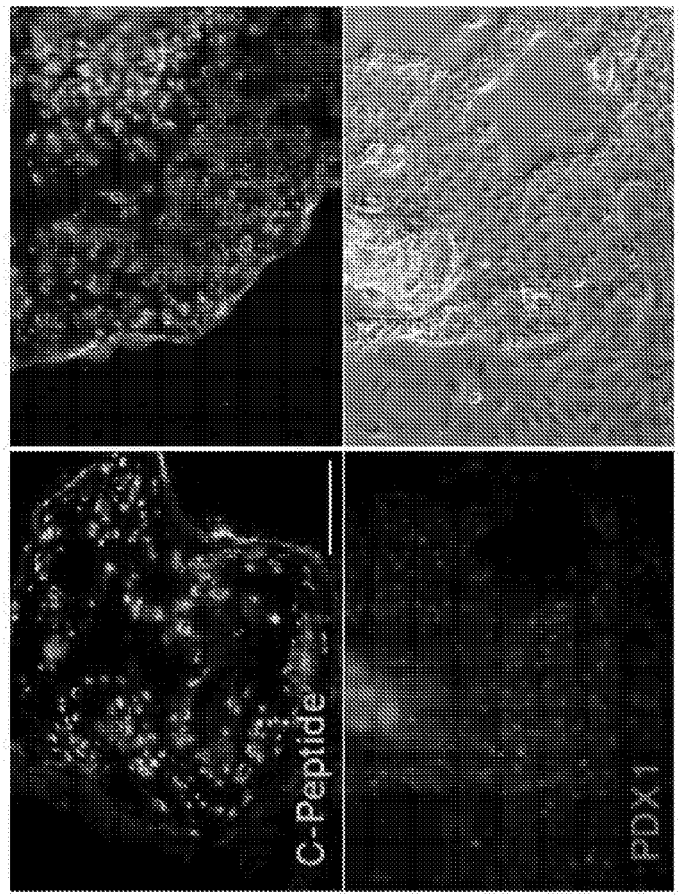

FIGs. 6A-E
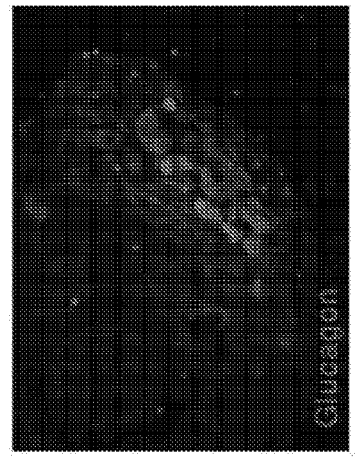
FIG. 6C
FIG. 6B
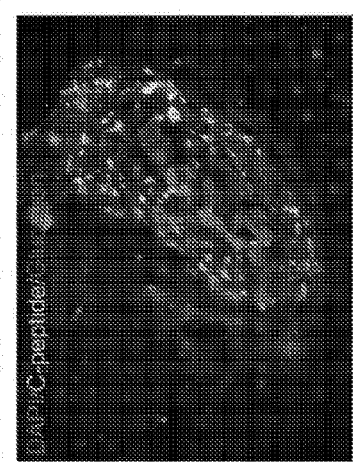
FIG. 6E
FIG. 6A
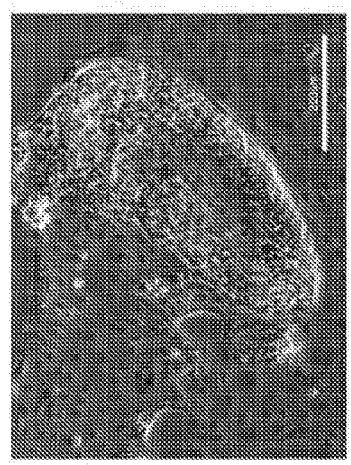
FIG. 6D

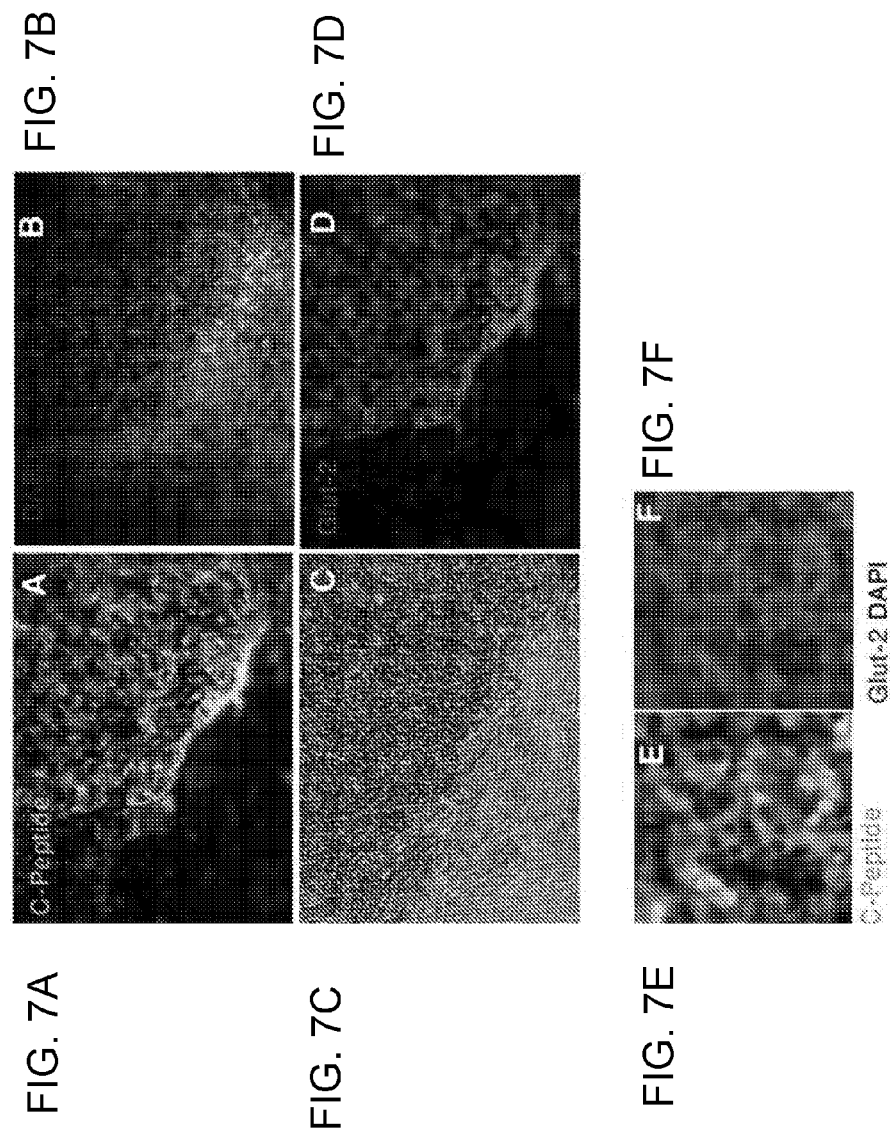

FIGs. 8A-F

FIGs. 9A-B

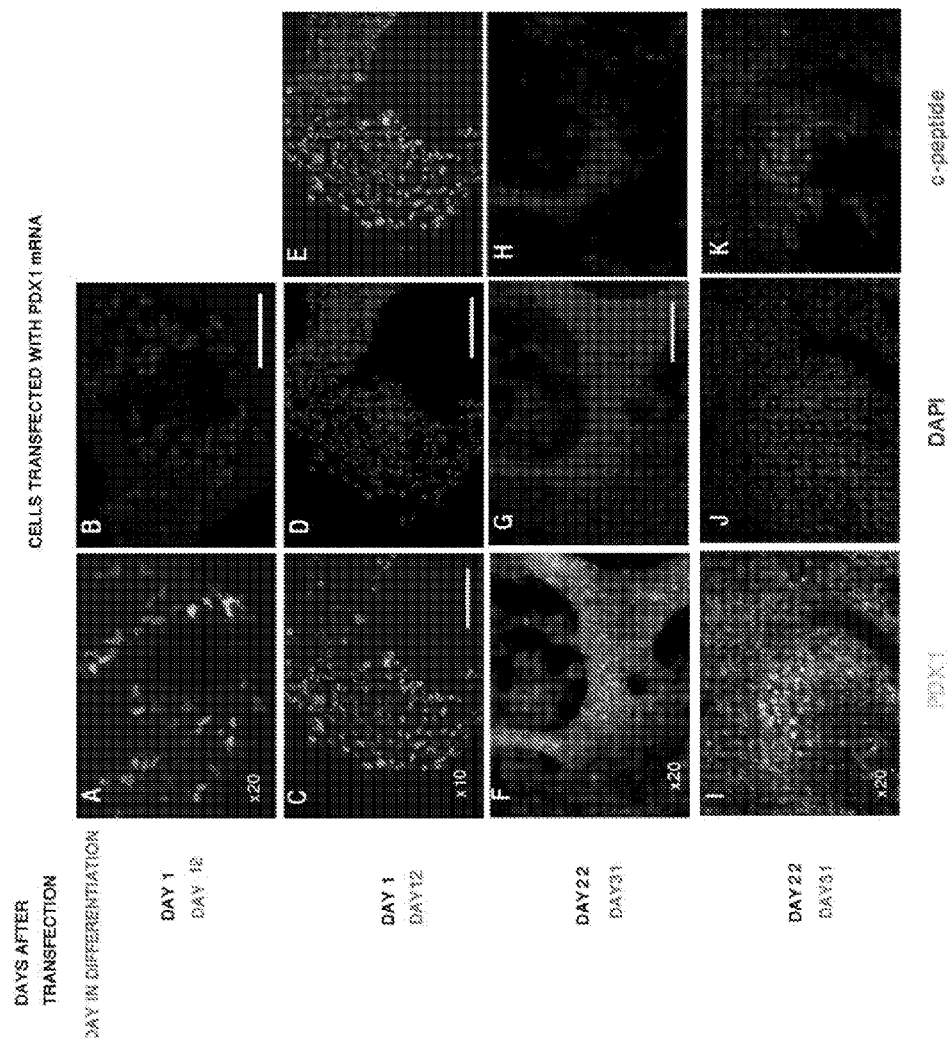
FIGs. 11A-K

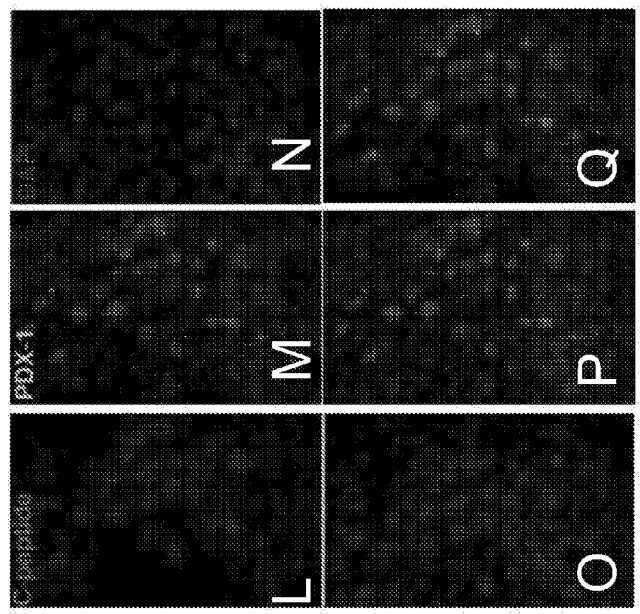
FIGs. 11L-Q

FIGs. 12A-J
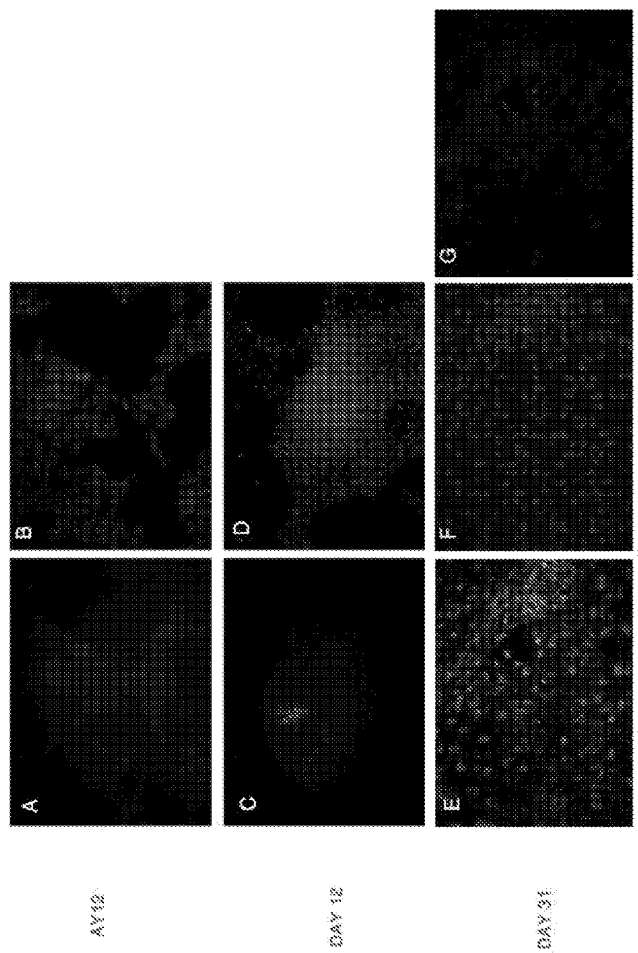
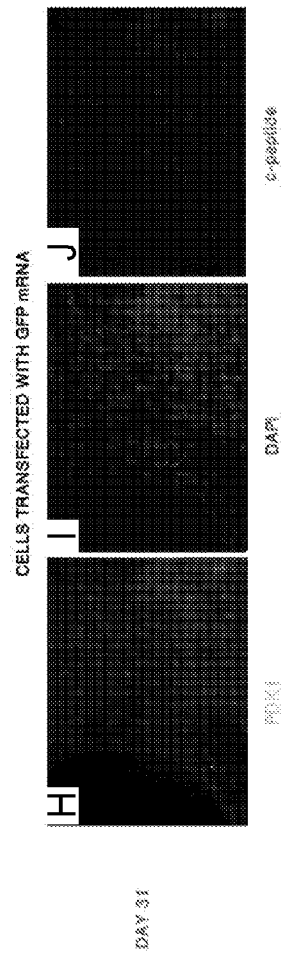

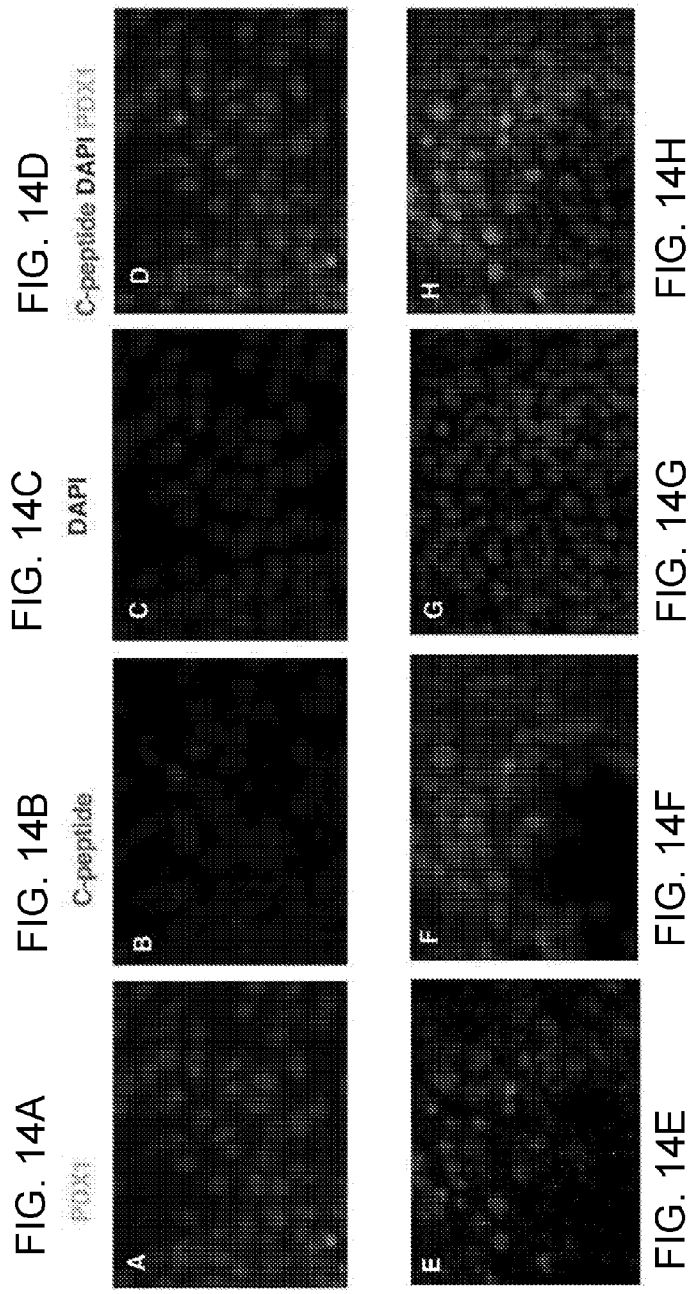
FIGs. 14A-H

FIGs. 16A-C

Without EDTA With 1mM EDTA

With 1mM EDTA

FIGs. 20A-D
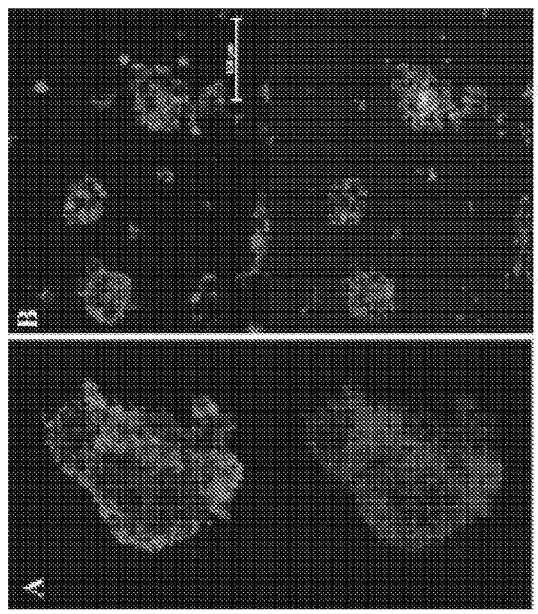
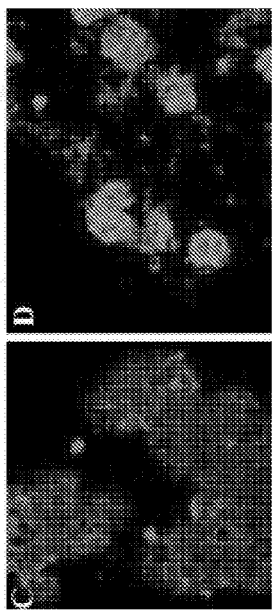
FIG. 20A FIG. 20B FIG. 20C FIG. 20D

INSULIN PRODUCING CELLS DERIVED FROM PLURIPOTENT STEM CELLS

CROSS-REFERENCE TO RELATED APPLICATIONS

This application is a National Phase Application of PCT International Application No. PCT/IL2011/050068, International Filing Date Dec. 15, 2011, entitled "INSULIN PRODUCING CELLS DERIVED FROM PLURIPOTENT STEM CELLS", published on Jun. 21, 2012 as International Publication No. WO 2012/081029, which claims priority from U.S. Provisional Application No. 61/423,171, filed on Dec. 15, 2010, both of which are incorporated herein by reference in their entirety.

FIELD AND BACKGROUND OF THE INVENTION

The present invention, in some embodiments thereof, relates to insulin-producing cells derived from pluripotent stem cells, and methods of generating same.

In type I diabetes, the insulin producing cells, or beta (β)-cells in the islets of Langerhans, are destroyed. Islets of Langerhans are specialized cell aggregates constituting the endocrine pancreas, including β-cells producing insulin (about 55% of the endocrine pancreas in humans), α-cells producing glucagon (about 35% in humans), δ-cells producing somatostatin (3-10%), PPcells producing pancreatic polypeptides (3-5%), and ε-cells producing grehlin (less than 1%). Insulin and glucagon are major regulators of blood glucose levels. In response to high glucose levels, insulin stimulates the uptake of glucose by body cells, fat, liver and muscle cells in particular, where it is converted into energy or stored into fat and glycogen, and therefore lowers the blood glucose level. Glucagon, conversely, stimulates the release of glucose from fat and from glycogen stores in situations of hypoglycemia.

Type I diabetes patients are dependent on injections of insulin to lower their blood glucose level. However, over years, the poor coordination between blood glucose levels and insulin levels often leads to severe deterioration of the patient's health. The physiological regulation of blood glucose as well as general health of such patient can be very much improved by the transplantation of human islets from cadavers. However the need for such transplants is much larger than availability of islet cells from cadaveric donors. In fact only a few thousand transplantations can be done worldwide every year for a potential number of 15 million patients who could benefit from such treatment. There is therefore a need for additional sources of pancreatic islet cells.

Stem cells have been proposed as one such additional source.

For example, the epithelium of the pancreatic duct serves as a source of cells capable of islet neogenesis in the adult, and may constitute the pancreatic stem cells, from which normal renewal of islets occurs throughout life. However, the use of these cells as a source for generation of insulin-producing cells is limited by their low expansion capacity in tissue culture and slow differentiation rate into insulin-producing cells.

Recent studies have shown that tissue stem cells are capable of reprogramming using dominant genes which activate a cascade of developmental events. Thus, mouse [Ferber S. et al. (2000). Nat. Med. 6: 568-572] and Xenopus [Horb M E. Et al., (2003), Curr. Biol. 13: 105-115] liver cells, as well as rat enterocytes [Kojima H et al. (2002), Diabetes 51: 1398-1408] were shown to activate β-cell gene expression following the expression of pancreatic duodenal homeobox 1 (Pdx1), a homeobox factor which plays key roles in pancreas development and gene expression in mature β cells [Jonsson J. et al., (1994) Nature 371: 606-609].

In addition, cultured human fetal liver cells modified by the expression of the Pdx1 gene were shown to produce and store mature insulin in significant amounts, release it in response to physiological glucose levels and replace β-cell function in streptozotocin (STZ)-diabetic non-obese diabetic severe combined immunodeficiency (NOD-scid) mice [Zalzman M. et al., (2003). Proc Natl Acad Sci USA 100: 7253-7258]. These cells expressed multiple β-cell genes, as well as genes of other islet cells and the exocrine pancreas, but continued to express some hepatic genes.

Human embryonic stem cell (hES), established as permanent cell lines from pluripotent human blastocyst inner cell mass, are capable of almost unlimited proliferation in vitro. In vitro, these cells are able to transit through early stages of embryonic development, including all pancreatic lineages. They are the potential source of huge amounts of transplantable donor cells needed for tissue regeneration. The ability to differentiate hESCs into beta-cells highlights a promising strategy to beta-cells replacement [Bernardo et al., 2009, Stem cells (Dayton, Ohio) 27, 341-351; D'Amour et al., 2006, Nature biotechnology 24, 1392-1401; Eshpeter et al., 2008, Cell proliferation 41, 843-858; Jiang et al., 2007, Stem cells (Dayton, Ohio) 25, 1940-1953; Kroon et al., 2008, Nature biotechnology 26, 443-452; Zhang et al., 2009, Cell research 19, 429-438, Sulzbacher et al, 2009, Stem Cell Rev, 5: 159-173].

U.S. Patent Application 20100255580 teaches methods of differentiating pluripotent stem cells towards the pancreatic lineage. However, up until presently directed differentiation of embryonic stem cells has generated cells that only produce low amounts of insulin, compared to beta cells. Therefore, there still remains a significant need to develop conditions for establishing a method of generating insulin-producing cells derived from pluripotent stem cells.

SUMMARY OF THE INVENTION

According to an aspect of some embodiments of the present invention there is provided a method of generating islet cells from pluripotent stem cells, the method comprising:

(a) culturing the pluripotent stem cells in a differentiation medium so as to differentiate the pluripotent stem cells into endoderm cells; and (b) culturing the endoderm cells in a medium comprising at least one growth factor, a cAMP inducer and retinoic acid (RA), the at least one growth factor being selected from the group consisting of FGF10, bFGF and FGF7 so as to generate further differentiated cells; and (c) culturing the further differentiated cells in a medium comprising a maturation factor selected from the group consisting of nicotinamide, GLP-1 and exendin 4, thereby generating islet cells from pluripotent stem cells.

According to an aspect of some embodiments of the present invention there is provided a method of generating islet cells from pluripotent stem cells, the method comprising:

(a) culturing the pluripotent stem cells in a differentiation medium comprising activin A so as to differentiate the pluripotent stem cells into endoderm cells; and (b) transfecting the endoderm cells with pdx-1 mRNA to generate further differentiated cells; and (c) culturing the further differentiated cells in a medium comprising a maturation factor selected from the group consisting of nicotinamide, exendin 4 and GLP-1, thereby generating islet cells from pluripotent stem cells.

According to an aspect of some embodiments of the present invention there is provided a method of generating islet progenitor cells from pluripotent stem cells, the method comprising:

(a) culturing the pluripotent stem cells in a differentiation medium so as to differentiate the pluripotent stem cells into endoderm cells; and (b) culturing the endoderm cells in a medium comprising at least one growth factor, a cAMP inducer and retinoic acid (RA), the at least one growth factor being selected from the group consisting of FGF10, bFGF and FGF7 so as to generate islet progenitor cells.

According to an aspect of some embodiments of the present invention there is provided a population of islet cells generated according to the methods described herein.

According to an aspect of some embodiments of the present invention there is provided a population of islet progenitor cells generated according to the methods described herein.

According to an aspect of some embodiments of the present invention there is provided a pharmaceutical composition comprising the population of cells described herein as an active ingredient and a pharmaceutically acceptable carrier.

According to an aspect of some embodiments of the present invention there is provided a method of treating Diabetes in a subject in need thereof, the method comprising transplanting a therapeutically effective amount of the population of cells described herein into the subject, thereby treating the Diabetes.

According to some embodiments of the invention, the differentiation medium comprises activin A.

According to some embodiments of the invention, the differentiation medium comprises serum.

According to some embodiments of the invention, the differentiation medium is devoid of serum.

According to some embodiments of the invention, the medium of step (b) further comprises noggin.

According to some embodiments of the invention, the differentiation medium comprises serum replacement substitute.

According to some embodiments of the invention, the differentiation medium further comprises Wnt3.

According to some embodiments of the invention, the culturing the pluripotent stem cells is effected by culturing collagenase-detached clusters of pluripotent stem cells on a gelatin coated surface.

According to some embodiments of the invention, the pluripotent stem cells comprise human embryonic stem cells.

According to some embodiments of the invention, the pluripotent stem cells comprise human induced pluripotent cells (iPP) cells.

According to some embodiments of the invention, the method further comprises culturing the endoderm cells in a medium comprising the at least one growth factor and the cAMP inducer, the medium being devoid of RA following step (a) and prior to step (b).

According to some embodiments of the invention, the cAMP inducer comprises forskolin.

According to some embodiments of the invention, the method further comprising:

(d) contacting said islet cells with an agent that binds to EpCAM following step (c); and (e) selecting cells which bind to the agent.

According to some embodiments of the invention, the method further comprises dispersing the islet cells following step (c) and prior to said contacting to generate dispersed islet cells.

According to some embodiments of the invention, the method further comprises re-aggregating said dispersed islet cells following the selecting.

According to some embodiments of the invention, the re-aggregating is effected in a presence of an agent that chelates calcium.

According to some embodiments of the invention, the agent that chelates calcium is selected from the group consisting of EDTA, EGTA, BAPTA, citrate, and phosphate.

According to some embodiments of the invention, the method further comprises seeding the dispersed islet cells on a scaffold following the contacting.

According to some embodiments of the invention, the re-aggregating is effected in a medium comprising glucose which is lower than that used in steps (a), (b) or (c).

According to some embodiments of the invention, the glucose concentration of each of the media is between 5 mM-100 mM.

According to some embodiments of the invention, the generating islet cells is effected without the generation of embryoid bodies.

According to some embodiments of the invention, the islet cells synthesize insulin.

According to some embodiments of the invention, the islet cells are glucose responsive.

According to some embodiments of the invention, the islet cells further synthesize glucagon.

According to some embodiments of the invention, the islet cells further synthesize somatostatin.

According to some embodiments of the invention, the endoderm cells are characterized by expression of Sox17 and FoxA2.

According to some embodiments of the invention, the endoderm cells do not express Oct4.

According to some embodiments of the invention, the method further comprises transfecting the further differentiated cells with a mRNA encoding a differentiating factor selected from the group consisting of Pancreatic and duodenal homeobox 1 (pdx1), neurogenin 3 (ngn3), paired box gene 4 (pax4), Homeobox protein Nkx-2.2 (nkx2.2), Homeobox protein NK-6 homolog A (nkx6.1) and v-maf musculoaponeurotic fibrosarcoma oncogene homolog A (MAF-A) following step (b) and prior to step (c).

According to some embodiments of the invention, the step (a) is effected for about 5 days.

According to some embodiments of the invention, the step (b) is effected for about 5 days.

According to some embodiments of the invention, the culturing is effected by about 2 days.

According to some embodiments of the invention, the population of cells is not genetically modified.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F are photographs illustrating that following five days Activin A conditioning, most of the ES cells acquire the definitive endoderm markers FoxA2 and Sox17. The picture shows staining with anti FoxA2 (HNF3b) and anti Sox17 antibodies. The scale bar represents 200 μm (FIGS. 1A and D), and 100 μm (FIGS. 1B, C, E and F). Counting the positive nuclei relatively to total cell nuclei stained with DAPI at high magnification allows evaluating the yield of cells expressing FoxA2 (89%) or Sox17 (98%).

FIG. 2A show a domain where cells, detected by DAPI staining, are attached as a monolayer and almost uniformly stained with anti Pdx1 antibody, the staining being located in the nucleus The morphology of the same domain at 2× higher enlargement is shown in FIGS. 2B-E, while superimposition of DAPI and Pdx1 staining (FIG. 2B) shows that the Pdx1 staining is nuclear.

FIGS. 2F and 2G show respectively Pdx1 staining and superimposition of Pdx1 staining and C-peptide staining. Pdx1 is localized in cell nuclei, and C-peptide in cytoplasmic domains of the cells. The cell morphology in this area (flat with bumping nuclei (FIG. 2H)) is similar to the cell morphology of Pdx1 positive cells at day 14.

FIGS. 3A-D are photographs illustrating that ITS, Nicotinamide and exendin-4 at 5 ng/ml cause rearrangement of the monolayer and formation of Pdx1 positive 3D clusters. The pictures were taken from day 32 of the differentiation protocol. From day 25 of differentiation, the monolayer tears out and epithelial buds (with high cell density) surge out of islands of the monolayer. On day 32, the epithelial buds are typically Pdx1 positive. In FIGS. 3A and B, the plate was treated with Nicotinamide and exendin-4, 5 ng/ml, for 20 days. As shown, the monolayer and the buds are both Pdx1 positive. In FIGS. 3C, D, the plate was treated only with Nicotinamide. The monolayer is less Pdx1 positive than in plates in which exendin-4 is used.

FIGS. 5A-D are photographs illustrating that both the monolayer and the budding areas contain C-peptide and Pdx1-positive domains. Pictures are from day 37 of the differentiation process. The cells in this picture were treated for the last 25 days with Nicotinamide and with 50 ng/ml exendin-4 from day 13 to day 29. FIGS. 5A-B show that C-peptide positive areas are either isolated from the rest of the cells (FIG. 5A), or in extended domains containing an area more densely populated (FIG. 5B). FIGS. 5C-D show a typical area containing Pdx1 positive cells (FIG. 5C) also as a bright field picture (FIG. 5D).

FIGS. 6A-E are photographs illustrating islet like domains contain C-peptide and glucagon-positive cells. Cells in this picture are on day 37 of the differentiation process. Cells seen here were treated with nicotinamide and 5 ng/ml of exendin-4 from day 13 and on. An islet-like structure is shown. C-peptide positive areas (green) are more highly densed populated domains that contour the islet like structure. Glucagon positive cells (red) are in the middle of these islet-like structures.

FIGS. 7A-G are photographs illustrating that C-peptide positive cells are also positive for the glucose receptor Glut-2, and Pdx1 positive on the 56$^{th}$ day of differentiation. At differentiation day 7, the colonies' cores were re-plated on new gelatin plates and their differentiation was continued under the normal protocol (RA then Exendin-4 (5 ng/ml from day 13 to day 29) and nicotinamide from day 13 and on). FIG. 7E is an enlargement of a detail of FIG. 7A. FIG. 7F shows that C-peptide and Glut-2 staining co-localize in cytoplasm and peripheral membranes, FIG. 7G illustrates that at day 56, Pdx1 is present in the nucleus of all the C-peptide positive cells.

FIGS. 8A-F are photographs illustrating that C-peptide-positive areas reorganize into three-dimensional structures after 60 days of differentiation. The pictures show C-peptide positive areas following 60 days of high exendin concentration treatment (50 ng/ml exendin-4 from day 13 and on). FIGS. 8A-C represent the same area respectively in normal light (FIG. 8A), immuno-staining with anti-C-peptide antibody (FIG. 8B), and overlay of the C-peptide and DAPI staining (FIG. 8C). FIGS. 8E-G represent a similar area respectively (FIG. 8D, DAPI staining, FIG. 8E, immuno-staining with anti-C-peptide antibody, and FIG. 8F, overlay of the C-peptide and DAPI staining).

FIG. 9A) and the surface of the culture which is C-peptide positive (Area; FIG. 9B).

FIGS. 11A-Q are photographs illustrating that Pdx1 mRNA transfection following Activin A treatment, circumvents the need for retinoic acid treatment. Pdx1 mRNA transfection following Activin A treatment induces the expression of Pdx1 protein in short term (12 days of differentiation) that persists at 31 days of differentiation. As a consequence of Pdx-1 transfection C-peptide expression is elevated at day 31, without the need for retinoic acid treatment. In FIGS. 11A-E areas of the culture 24 hour after the last transfection (day 12 of differentiation) are shown. Pdx1 expression is strong and is visible in most colonies. Pdx1 labeling is more intense at the border of the colonies (FIG. 11E). FIGS. 11F-H and 11I-K represent randomly chosen distinct areas of the Pdx1 mRNA transfected wells, fixed 22 days after the last transfection (day 32 of the differentiation). The Pdx1 positive areas are very densely populated (FIGS. 11F, I), and a large proportion of these cells are also C-peptide positive (FIGS. 11H, K). FIGS. 11L-Q show an enlargement of an area of FIG. 11K, to demonstrate that at day 31 of the differentiation and day 22 following transfection with Pdx1 mRNA, the Pdx1 protein is expressed in nuclei, the c-peptide in the cytoplasm of the same cells.

FIGS. 12A-J are photographs illustrating that Activin A treated cells, devoid of both RA treatment and Pdx1 transfection poorly express Pdx1. Activin A treated cells grown without RA and without Pdx1 transfection, have negligible numbers of Pdx1 positive cells on 12th day of differentiation, and do not differentiate into C-peptide positive cells on day 31. Cells not transfected with Pdx1 mRNA, and not treated with retinoic acid, were fixed on day 12 of culture (FIGS. 12A-D) (compare with samples transfected with Pdx1 mRNA at same time (FIGS. 11A-E). The area labeled with Pdx1 antibody is negligible. After thirty-one day of differentiation, (E-G), the weakly Pdx1 positive areas are poorly populated and do not stain for C-peptide. FIGS. 12H-J are control experiments transfecting GFP mRNA instead of Pdx1 mRNA.

In FIG. 13A, the ratios of C-peptide positive cells over Pdx1-positive cells were estimated using the program Image Pro. The program was run on 20 fields of Pdx1 positive cells among Pdx1 mRNA transfected cells, or among GFP-mRNA transfected cells (control cells). FIG. 13A demonstrates that exogeneously added Pdx1 mRNA markedly increases the percent of Pdx1 positive cells that become insulin producing cells as measured by C-peptide staining FIG. 13B shows that Pdx1 mRNA transfection not only increases the ratio of C-peptide positive cells out of Pdx-1 positive cells but also the ratio C-peptide positive cells out of total cells (Dapi stained).

FIGS. 14A-H are photographs illustrating that C-peptide positive cells 22 days after transfection with Pdx-1 mRNA are strongly Pdx-1 positive. Two domains of Pdx-1 positive cells are shown. FIGS. 14A-D show a domain including large hexagonal cells with a flat nucleus, where most of the cells are Pdx1 positive. These cells are not C-peptide positive and represent progenitors. FIGS. 14E-H show a domain where cell population is dense, and most of the cells are very strongly C-peptide positive. A strong staining with PDX1 antibody is noticed in most of the C-peptide positive cell nuclei.

In FIG. 18D, cells were reacted with anti-EpCam antibodies (green) and anti-Glucagon antibodies (red).

FIGS. 20A-D are photographs illustrating that re-aggregation of EpCam positive cells in the presence of EDTA affects the size of the aggregates and the ratio of c-peptide positive cells relative to negative cells. Cells differentiated for 20 days were dissociated and EpCam positive cells were selected and cultured in suspension for 3 days in conditions for re-aggregation, without (A, C) or with 1 mM EDTA (B, D). The cells were reacted with anti-c-peptide antibodies MC AbCAm 1975 (A, B, red) or anti EpCam antibody CD326 linked to PE (C, D red).

DESCRIPTION OF SPECIFIC EMBODIMENTS OF THE INVENTION

Figure 2B:
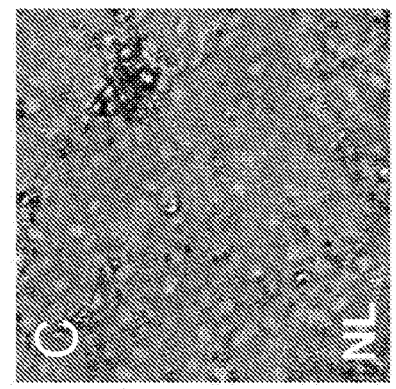
FIGS. 2A-E are photographs illustrating induction of Pdx1 after treatment with Activin A and retinoic acid/ATRA (day 14).
Figure 2C:
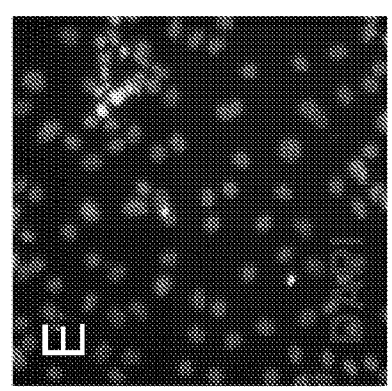
Figure 2D:
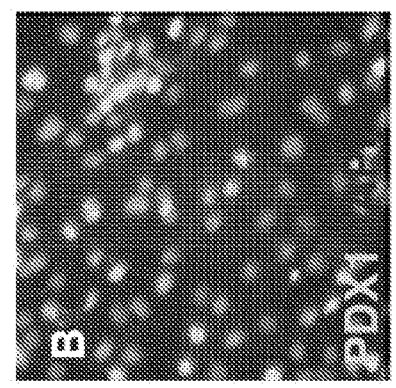
Figure 2E:
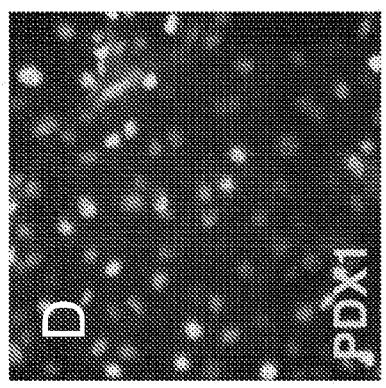
Figure 2A:
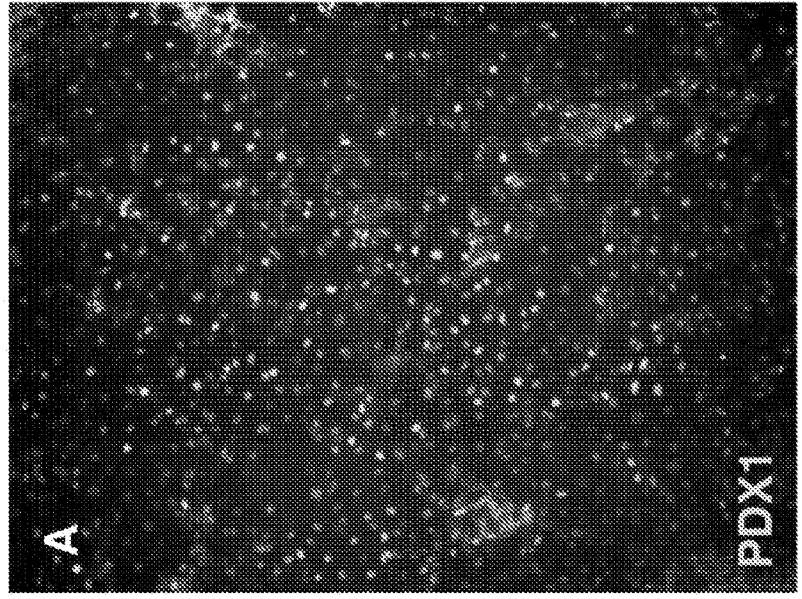
Figure 2F:
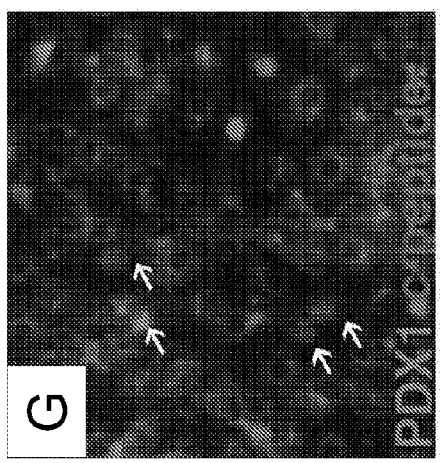
FIGS. 2F-I show Pdx1 and C-peptide staining at day 21 of the differentiation.
Figure 2G:
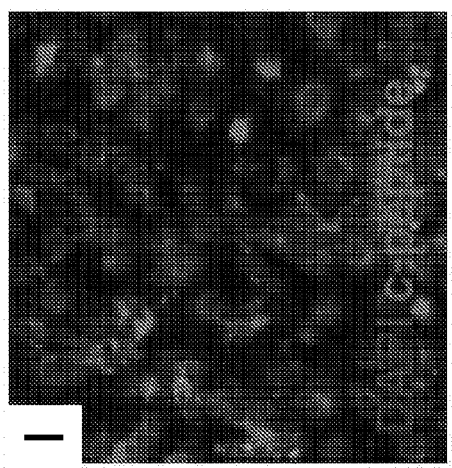
Figure 2H:
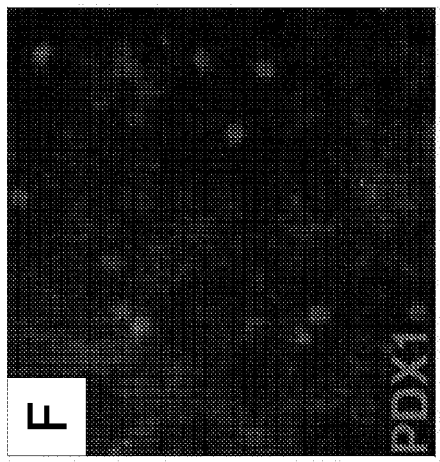
Figure 2I:
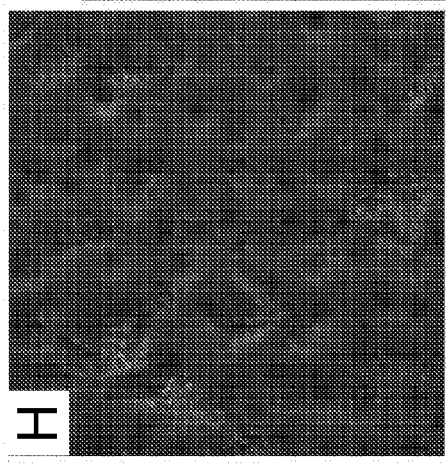

The present invention, in some embodiments thereof, relates to insulin-producing cells derived from pluripotent stem cells, and methods of generating same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Type I diabetes is caused by the autoimmune destruction of the pancreatic islet insulin-producing beta cells. Insulin administration does not prevent the long-term complications of the disease, since the optimal insulin dosage is difficult to adjust. Replacement of the damaged cells with regulated insulin-producing cells is considered the ultimate cure for type 1 diabetes. Pancreas transplantation has been successful but is severely limited by the shortage of donors.

An alternative to forced expansion of post-mitotic β cells is the induction of differentiation of stem cells, (which have a natural self-expansion capacity), into insulin-producing cells. Various groups have suggested different differentiation protocols based on the normal differentiation pathways that operate during intra-uterine development (see for example D'Amour, Nature Biotechnology 2006; Jiang, Stem cells, 2007; an Kroon Nature Biotechnology 2008). However, up until presently directed differentiation of embryonic stem cells has generated cells that only produce low amounts of insulin, compared to beta cells.

In an attempt to generate populations of cells that would be effective for treating Diabetes, the present inventors devised novel differentiation protocols and demonstrated that the generated cells synthesized high levels of both insulin and glucagon as illustrated in FIGS. 4-11,18 and Table 4.

Specifically, the present inventors showed by double staining for insulin C-peptide and for glucagon, that about one third of the cells in the generated islets produce glucagon (alpha-cell phenotype) and two third produce insulin (beta cell phenotype)—FIGS. 6A-E. The differentiation process reproduces therefore the structure of natural pancreatic islets of Langerhans.

Thus, according to one aspect of the present invention there is provided a method of generating islet cells from pluripotent stem cells, the method comprising:

(a) culturing the pluripotent stem cells in a differentiation medium so as to differentiate the pluripotent stem cells into endoderm cells; and (b) culturing the endoderm cells in a medium comprising at least one growth factor, a cAMP inducer and retinoic acid (RA), the at least one growth factor being selected from the group consisting of FGF10 and FGF7 so as to generate further differentiated cells; and (c) culturing the further differentiated cells in a medium comprising a maturation factor selected from the group consisting of nicotinamide, GLP-1 and exendin 4, thereby generating islet cells from pluripotent stem cells.

As used herein, the phrase "islet cells" refers to a cell that synthesizes at least one of the following islet-specific polypeptide hormones—insulin, glucagon, somatostatin and pancreatic polypeptide. Thus, the islet cells generated according to the methods of the present invention may be construed as beta cells that produce insulin; 2) alpha cells that produce glucagon; 3) delta cells (or D cells) that produce somatostatin; and/or F cells that produce pancreatic polypeptide.

Typically the islet cells of this aspect of the present invention store the hormones in secretary vesicles in the form of secretory granules.

As mentioned herein above, the present inventors have shown that using the methods of the present invention populations of islet cells may be generated, the relative amounts of each cell type reflecting those in naturally occurring islets (i.e. two thirds insulin producing cells and one third glucagon producing cells).

The phrase "pluripotent stem cells" as used herein, refers to cells which are capable of differentiating into the three embryonic germ cell layers, i.e., endoderm, ectoderm and mesoderm.

According to one embodiment, the pluripotent stem cells comprise embryonic stem cells and/or induced pluripotent stem cells.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst (see WO2006/040763) and embryonic germ (EG) cells which are obtained from the genital tissue of a fetus any time during gestation, preferably before 10 weeks of gestation.

Induced pluripotent stem cells (iPS; embryonic-like stem cells), are cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell.

The embryonic stem cells of the present invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells can also be used with this aspect of the present invention. Human ES cells can be purchased from the NIH human embryonic stem cells registry (http://escr.nih.gov). Non-limiting examples of commercially available embryonic stem cell lines are BG01, BG02, BG03, BG04, CY12, CY30, CY92, CY10, TE03 and TE32.

In addition, ES cells can be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, Mo., USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090,622.

Induced pluripotent stem cells (iPS) (embryonic-like stem cells) can be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1): 39-49; Aoi T, et al., Generation of Pluripotent Stem Cells from Adult Mouse Liver and Stomach Cells. Science. 2008 Feb. 14. (Epub ahead of print); IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear transfer into zygotes if the recipient cells are arrested in mitosis.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernable cell junctions. Additional features of undifferentiated stem cells are further described herein under.

Currently practiced ES culturing methods are mainly based on the use of feeder cell layers which secrete factors needed for stem cell proliferation, while at the same time, inhibit their differentiation. Feeder cell free systems have also been used in ES cell culturing, such systems utilize matrices supplemented with serum, cytokines and growth factors as a replacement for the feeder cell layer.

Feeder-Layer Based Cultures

Mouse Feeder Layers—

The most common method for culturing ES cells is based on mouse embryonic fibroblasts (MEF) as a feeder cell layer supplemented with tissue culture medium containing serum or leukemia inhibitor factor (LIF) which supports the proliferation and the pluripotency of the ES cells [Thomson J A, Itskovitz-Eldor J, Shapiro S S, Waknitz M A, Swiergiel J J, Marshall V S, Jones J M. (1998). Embryonic stem cell lines derived from human blastocysts. Science 282: 1145-7; Reubinoff B E, Pera M F, Fong C, Trounson A, Bongso A. (2000). Embryonic stem cell lines from human blastocysts: somatic differentiation in vitro. Nat. Biotechnol. 18: 399-404]. MEF cells are derived from day 12-13 mouse embryos in medium supplemented with fetal bovine serum. Under these conditions mouse ES cells can be maintained in culture as pluripotent stem cells, preserving their phenotypical and functional characteristics. However, unlike mouse ES cells, the presence of exogenously added LIF does not prevent differentiation of human ES cells. Furthermore, the use of feeder cells substantially increases the cost of production, and makes scale-up of human ES cell culture impractical. Additionally, the feeder cells are metabolically inactivated to keep them from outgrowing the stem cells, hence it is necessary to have fresh feeder cells for each splitting of human ES culture. Since at present, the separation of feeder cell components from embryonic cells prepared in bulk culture cannot be efficiently achieved, feeder cell layer-prepared ES cultures are not suitable for human therapy.

ES cells can also be cultured on MEF under serum-free conditions using serum replacement supplemented with basic fibroblast growth factor (bFGF) [Amit M, Carpenter M K, Inokuma M S, Chiu C P, Harris C P, Waknitz M A, Itskovitz-Eldor J, Thomson J A. (2000). Clonally derived human embryonic stem cell lines maintain pluripotency and proliferative potential for prolonged periods of culture. Dev. Biol. 227: 271-8]. Under these conditions the cloning efficiency of ES cells is 4 times higher than under fetal bovine serum. In addition, following 6 months of culturing under serum replacement the ES cells still maintain their pluripotency as indicated by their ability to form teratomas which contain all three embryonic germ layers. Although this system uses a better-defined culture conditions, the presence of mouse cells in the culture exposes the human culture to pathogens which restricts their use in cell-based therapy.

Human Embryonic Fibroblasts or Adult Fallopian Epithelial Cells as Feeder Cell Layers—

Human ES cells can be grown and maintained using human embryonic fibroblasts, cord blood fibroblasts or adult fallopian epithelial cells. When grown on these human feeder cells the human ES cells exhibit normal karyotypes, present alkaline phosphatase activity, express Oct-4 and other embryonic cell surface markers including SSEA-3, SSEA-4, TRA-1-60, and GCTM-2, form teratomas in vivo, and retain all key morphological characteristics [Richards M, Fong C Y, Chan W K, Wong P C, Bongso A. (2002). Human feeders support prolonged undifferentiated growth of human inner cell masses and embryonic stem cells. Nat. Biotechnol. 20: 933-6].

Foreskin Feeder Layers—

Human ES cells can be cultured on human foreskin feeder layer as disclosed in U.S. patent application Ser. No. 10/368, 045. Foreskin derived feeder cell layers consist of a complete animal-free environment suitable for culturing human ES cells. In addition, foreskin cells can be maintained in culture for as long as 42 passages since their derivation, providing the ES cells with a relatively constant environment. Under these conditions the human ES cells were found to be functionally indistinct from cells grown with alternate protocols (e.g., MEF). Following differentiation, ES cells expressed genes associated with all three embryonal germ layers, in vitro, and formed teratomas in vivo, consisting of tissue arising from all three germ layers. In addition, unlike human fallopian epithelial cells or human embryonic fibroblasts, human ES cells cultured on foreskin feeder layers were maintained in culture in a pluripotent and undifferentiated state for at least 87 passages.

Feeder-Free Cultures

Stem cells can be grown on a solid surface such as an extracellular matrix (e.g., Matrigel® or laminin) in the presence of a culture medium.

Following expansion of the pluripotent stem cells, the present invention contemplates culture thereof in a differentiation medium so as to differentiate the pluripotent stem cells into endoderm cells.

The present invention contemplates culturing the pluripotent stem cells under adherent conditions (attached to extracellular matrix or gelatin coated plates) or under suspension (in non tissue culture-treated plates). Contemplated extracellular matrices include, but are not limited to MATRIGEL® (Becton Dickenson), laminin, fibronectin, proteoglycan, entactin, heparan sulfate, and the like, alone or in various combinations An "adherent culture" refers to a culture in which cells in contact with a suitable growth medium are present, and can be viable or proliferate while adhered to a substrate. A "non-adherent culture" refers to a culture in which cells are typically in suspension with a suitable growth medium, and can be viable or proliferate while not being adhered to a substrate.

According to one embodiment, the pluripotent stem cells are first detached from their original surface of irradiated fibroblasts (on which they were expanded)—e.g. by using collagenase and then replated on a different adherent surface for differentiation (e.g. gelatin coated surface).

According to another embodiment, the pluripotent stem cells are differentiated on the same surface of irradiated fibroblasts on which they were expanded.

The phrase "endoderm cells" refers to a population of cells wherein at least 50% thereof, more preferably at least 70% thereof express at least one of the two markers Sox17 or FoxA2. According to a preferred embodiment, less than 20% of the cells, more preferably less than 10% of the cells express markers for pluripotency, e.g. Oct4.

Methods of determining expression levels of Sox17, FoxA2 or Oct4 are known in the art and include for example RT-PCR, Immunohistochemistry and the like.

Methods of generating endoderm cells from pluripotent stem cells are known in the art and include for example use of Nodal (NM_018055; NP_060525.3) and small molecules (see for example Borowiak et al Cell Stem Cell, Volume 4, Issue 4, 348-358, 3 Apr. 2009. Alternatively, endoderm cells may be generated via embryoid bodies. Specifically, hES cells may be cultured in suspension without FGF to generate embryoid bodies. The endodermal cells may be selected out of the EBs, see for example (Segev, Fischman, Ziskind et al., Stem cells, 2004; 22(3):265-74.

According to one embodiment the differentiation into endodermal cells is carried out in the presence of activin A.

Exemplary concentration ranges of activin A include 1-500 ng/ml, more preferably 1-250 ng/ml, more preferably 50-200 ng/ml, such as for example 100 ng/ml.

According to a particular embodiment of this aspect of the present invention, the pluripotent stem cells are differentiated into ectodermal cells by initial culture (e.g. for about 2 days) in a medium comprising activin A and a Wnt ligand and subsequent culture (e.g. 1 day) in a medium comprising activin A, but devoid of Wnt-3.

Typically, in the first culture medium there may be a lower concentration of serum, relative to the second culture medium. Increasing the serum concentration in the second culture medium increases the survival of the cells, or, alternatively, may enhance the proliferation of the cells. The serum concentration of the first medium may be in the range of about 0% to about 10%. Alternatively, the serum concentration of the first medium may be in the range of about 0% to about 2%. Alternatively, the serum concentration of the first medium may be in the range of about 0% to about 1%. Alternatively, the serum concentration of the first medium may be about 0.5%.

According to a particular embodiment, both the first culture medium and the second culture medium are devoid of serum. Typically, in place of serum a replacement is added. Such replacements may be provided at various concentrations, such as a concentration of at least 0.1%, e.g., a concentration of at least 0.2%, at least 1%, at least 1.5% or at least 2%. Serum replacements are widely available—for example from Invitrogen (Knock-Out Serum Replacement™ and Sigma-Aldrich). An additional agent that may be used to replace serum is albumin—for example human recombinant albumin.

The present inventors have shown that when serum is removed from the above described medium, the addition of noggin at a later stage has a synergistic effect on the amount of insulin produced in the cells. Typically, the noggin is added together with the growth factor, cAMP inducer and retinoic acid (i.e. stage (b) of the protocol), as further described herein below.

The choice of the Wnt ligand may be optimized to improve the efficiency of the differentiation process. The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

Contemplated culture mediums in which the differentiation process may be carried out include for example Dulbecco's modified Eagle's medium (DMEM), Gibco #11965-092; Knockout Dulbecco's modified Eagle's medium (KO DMEM), Gibco #10829-018; Ham's F12/50% DMEM basal medium, CMRL-1066. Preferably the culture medium is of medical grade purity. Typically the culture medium has a concentration of glucose between about 12 mM-100 mM, more preferably between about 15 mM-50 mM—e.g.17 mM.

The present inventors have discovered a novel cocktail of three agents which together can be used to differentiate endodermal cells towards a pancreatic lineage (i.e. into pancreatic progenitor cells).

The phrase "pancreatic progenitor cells" refers to a population of cells which are not fully differentiated into pancreatic cells, yet are committed to differentiating towards at least one type of pancreatic cell—e.g. beta cells that produce insulin; alpha cells that produce glucagon; delta cells (or D cells) that produce somatostatin; and/or F cells that produce pancreatic polypeptide.

Typically, pancreatic progenitor cells express some of the phenotypic markers that are characteristic of pancreatic lineages (e.g. GLUT2, PDX-1 Hnf3β, PC1/3, Beta2, Nkx2.2 and PC2). Typically, they do not produce progeny of other embryonic germ layers when cultured by themselves in vitro, unless dedifferentiated or reprogrammed. It will be appreciated that it is not implied that each of the cells within the population have the capacity of forming more than one type of progeny, although individual cells that are multipotent pancreatic progenitor cells may be present.

Thus, following differentiation of pluripotent cells to endoderm cells, the cells are subsequently differentiated in a medium comprising a fibroblast growth factor (e.g. FGF10, FGF7 or bFGF), a cAMP inducer and retinoic acid (RA). As mentioned, herein above, that when the initial culturing for the generation of endoderm cells, is effected in the absence of serum, the differentiation medium comprising the FGF, cAMP inducer and RA may also comprise noggin.

Contemplated concentration ranges of the fibroblast growth factor are between 50 µg/ml-50 µg/ml (e.g. 50 ng/ml).

The term "cAMP inducer" as used herein, refers to a compound that induces cAMP activity either directly by forskolin or NPA (R(−)-propylnorapomorphine a D2 receptor agonist of PICA, increases cAMP) or indirectly by inhibiting phosphodiesterase by Isobutyl-methoylxanthine (IBMX) or by compounds with IBMX like activity such as cAMP-specific Ro 20-1724, Rolipram, or Etazolate but more preferably selected from the group including Isobutyl-methoylxanthine (IBMX), or forskolin used alone or in combination.

A contemplated concentration range for forskolin is between 1-100 µM (e.g. 10 µM).

Retinoic acid may be used at a concentration between 1 nM-1 mM (e.g. 1-10 µm).

Contemplated concentration ranges of the noggin are between 50-500 ng/ml (e.g. 100 ng/ml). Noggin is commercially available from a number of sources—e.g. Preprotech.

Typically the differentiation process involving the cocktail described above is effected for about 2-10 days (e.g. five days). Typically, the noggin when added is added for the full length of this culturing step (e.g. for five days).

Prior to differentiation in the presence of the cocktail described above, the endoderm cells may be preconditioned for further differentiation in a medium comprising the FGF and cAMP inducer (without the retinoic acid). This preconditioning may be effected for between 1-5 days (e.g. 2 days).

The final differentiation step of the present protocol involves maturation in a medium comprising nicotinamide and/or exendin 4. This maturation step may last for 30-60 days.

Contemplated concentration ranges of nicotinamide are between 1-100 mM (e.g. 10 mM).

Contemplated concentration ranges of exendin-4 are between 1-100 ng/ml.

The present inventors have found that enrichment of insulin producing cells may be performed selected by selecting for cells expressing EpCAM.

Typically, the selecting is effected using antibodies that are capable of specifically recognizing this cell-surface protein, although the present invention contemplates additional agents such as polynucleotides or small molecules.

The enriching may be effected using known cell sorting procedures such as by using a fluorescence-activated cell sorter (FACS).

As used herein, the term "flow cytometry" refers to an assay in which the proportion of a material (e.g. renal cells comprising a particular maker) in a sample is determined by labeling the material (e.g., by binding a labeled antibody to the material), causing a fluid stream containing the material to pass through a beam of light, separating the light emitted from the sample into constituent wavelengths by a series of filters and mirrors, and detecting the light.

A multitude of flow cytometers are commercially available including for e.g. Becton Dickinson FACScan and FACScalibur (BD Biosciences, Mountain View, Calif.). Antibodies that may be used for FACS analysis are taught in Schlossman S, Boumell L, et al, [Leucocyte Typing V. New York: Oxford University Press; 1995] and are widely commercially available.

If the EpCAM antibody is attached to a magnetic moiety (either directly, or indirectly through a cognate binding molecule), the heterogeneous cell population may be enriched for EpCAM$^+$ cells by magnetic activated cell separation.

If the EpCAM antibody is attached is attached to an affinity moiety, the heterogeneous cell population may be enriched for EpCAM$^+$ cells by affinity purification with the cognate binding molecule. Thus, for example, if the EpCAM antibody is attached to biotin, the heterogenous cell population may be depleted of EpCAM$^+$ by purification with strepavidin beads or column. The EpCAM$^+$ cells can subsequently be retrieved. If, for example the EpCAM antibody is attached to an antibody or an Fc of an antibody, the heterogenous cell population may be depleted of EpCAM$^+$ by purification with protein A beads or column. The EpCAM$^+$ cells can subsequently be retrieved.

It will be appreciated that since the differentiated cells of this aspect of the present invention typically grow as adherent clusters, prior to cell sorting the heterogenous cell population should preferably be dispersed using a dispersing agent.

Examples of dispersing agents include, but are not limited to dispase, collagenase, accutase and trypsin. Alternatively, or additionally trituration may also be performed to increase the dispersal of the cells.

Following enrichment of EpCAM$^+$ cells, the cells are typically cultured for at least two more days, and preferably no more than 8 days (e.g. 2-6 days) under conditions that allow re-aggregation thereof. Typically, the cells are re-aggregated in a presence of an agent which inhibits calcium dependent cell-cell interactions. Examples of such agents include EDTA XXX are there any others you could use?

According to a particular embodiment, the re-aggregation is effected at low glucose concentrations (i.e. lower than the glucose concentration of the initial differentiation stages). Exemplary ranges of glucose that are contemplated by the present inventors include 1-10 mM, more preferably 2-8 mM—e.g. 5.5 mM.

In order for re-aggregation to take place, the cells may be cultured on culture dishes (e.g. low-adherent binding plates) or may be seeded on a solid support (i.e. scaffold, as further described herein below).

Typical scaffolds contemplated by the present invention include those that are fabricated from collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol).

According to one embodiment, the scaffold is fabricated from a biocompatible polymer.

The phrase "biocompatible polymer" refers to any polymer (synthetic or natural) which when in contact with cells, tissues or body fluid of an organism does not induce adverse effects such as immunological reactions and/or rejections and the like. It will be appreciated that a biocompatible polymer can also be a biodegradable polymer.

The phrase "biodegradable polymer" refers to a synthetic or natural polymer which can be degraded (i.e., broken down) in the physiological environment such as by proteases. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. Examples of biodegradable polymers include, but are not limited to, collagen (e.g., Collagen I or IV), fibrin, hyaluronic acid, polylactic acid (PLA), polyglycolic acid (PGA), polycaprolactone (PCL), poly(Lactide-co-Glycolide) (PLGA), polydioxanone (PDO), trimethylene carbonate (TMC), polyethyleneglycol (PEG), Collagen, PEG-DMA, Alginate, chitosan copolymers or mixtures thereof.

According to an exemplary embodiment, the scaffold comprises a porous alginate sponge.

The present inventors have also found that transfection of endodermal cells with mRNA encoding differentiating factors prior to or concomitant with step (c) of the differentiation process but following or concomitant with step (b) of the differentiation process may be useful for generating islet cells. The transfections may help to enrich the culture with cells at certain stages of differentiation.

Thus for example the present invention contemplates transfection with one of the following mRNA agents: Pancreatic and duodenal homeobox 1 (Pdx1), neurogenin 3 (Ngn3), paired box gene 4 (Pax4), Homeobox protein Nkx-2.2 (Nkx2.2), Homeobox protein NK-6 homolog A (Nkx6.1) and v-maf musculoaponeurotic fibrosarcoma oncogene homolog A (MAF-A).

Pdx1 mRNA or Neurogenin 3 (Ngn3) mRNA may be transfected together with the retinoic acid culturing step, prior to the retinoic acid treatment, or directly prior to the maturation step, avoiding the retinoic acid treatment. It will be appreciated that Pdx1 mRNA may be transfected together with Ngn3 mRNA.

Preferably, Paired box gene 4 (Pax4) mRNA transfection is effected no later than one day following retinoic acid culture.

Preferably, Homeobox protein Nkx-2.2 (Nkx2.2), Homeobox protein Nkx-6.1 homolog A (Nkx6.1) mRNA transfection is effected no later than 30 days following the end of retinoic acid treatment.

MAF-A mRNA transfection may be effected as late as 1 week following the retinoic acid culture stage.

The present inventors have found that Pdx-1 mRNA transfection may be used to replace the retinoic acid culture step (b) of the protocol, although it will be appreciated that it may also be effected at a later stage as well (i.e. following step (b) of the protocol), for example several days after maturation process have started e.g. at day 30 of differentiation.

Methods for transfection of mRNA are known in the art, including commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Methods of synthesizing mRNA in vitro are known in the art.

In a preferred embodiment, the mRNA has both a cap on the 5' end and a 3' poly(A) tail which determine ribosome binding, initiation of translation and stability of the mRNA in the cell.

The conventional method of integration of polyA/T stretches into a DNA template is molecular cloning. The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). Additionally, the attachment of different chemical groups to the 3' end can increase mRNA stability. Such attachment can contain modified/artificial nucleotides, aptamers and other compounds. For example, ATP analogs can be incorporated into the poly (A) tail using poly(A) polymerase. ATP analogs can further increase the stability of the RNA. Suitable ATP analogs include, but are not limited to, cordiocipin and 8-azaadenosine.

5' caps on also provide stability to RNA molecules. In a preferred embodiment, The 5' cap may, for example, be m$^7$G (5')ppp(5')G, m$^7$G(5')ppp(5')A, G(5')ppp(5')G or G(5')ppp (5')A cap analogs, which are all commercially available. The 5' cap can also be an anti-reverse-cap-analog (ARCA) (Stepinski, et al., RNA, 7:1468-95 (2001)) or any other suitable analog.

The RNAs may also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, Ngn-3, NeuroD and Islet-1.

Markers characteristic of cells of the beta cell lineage are well known to those skilled in the art, and additional markers characteristic of the beta cell lineage continue to be identified. These markers can be used to confirm that the cells treated in accordance with the present invention have differentiated to acquire the properties characteristic of the beta-cell lineage. Beta cell lineage specific characteristics include the expression of one or more transcription factors such as, for example, Pdx1 (pancreatic and duodenal homeobox gene-1), Nkx2.2, Nkx6.1, Is11, Pax6, Pax4, NeuroD, Hnf1b, Hnf-6, Hnf-3beta, and MafA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells expressing markers characteristic of the pancreatic endocrine lineage. Alternatively, the efficiency of differentiation may be determined by exposing a treated cell population to an agent (such as an antibody) that specifically recognizes a protein marker expressed by cells expressing markers characteristic of the beta cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Following differentiation and maturation the final product may be enriched for pancreatic islet cells, e.g. by using a computer-controlled robotic arm linked to a microscope in order to select and harvest the areas with islet morphology or alternatively by using FACS and selecting for a particular marker. This procedure avoids the risk of contamination with pluripotent ES cells and risks of teratoma after implantation of the cells in vivo.

The present inventors contemplate that the islet cells of the present invention are glucose responsive since the generated insulin expressing cells were shown to also express the glucose transporter transmembrane protein Glut-2, one of the proteins essential for the glucose-dependent insulin secretion (FIG. 7D). The glucose-responsiveness of the cells was further demonstrated in illustrated in FIG. 23A. According to this aspect of the present invention, the phrase "glucose responsive" refers to the ability of the differentiated cells of the present invention to secrete insulin in response to glucose. Preferably, the adult islet beta cells secrete at least twice the quantity of insulin in response to 16 mM glucose as they secrete at 0 mM glucose.

The population of adult islet beta cells of the present invention may be further modified (e.g. genetic modification) to express a pharmaceutical agent such as a therapeutic agent, a telomerase gene, an agent that reduces immune mediated rejection or a marker gene. It is contemplated that therapeutic agents such as antimetabolites (e.g., purine analogs, pyrimidine analogs), enzyme inhibitors and peptidomimetics may be generally useful in the present invention. An example of a gene that may reduce immune mediated rejection is the uteroglobin gene. Uteroglobin is a protein expressed during pregnancy that confers immunologic tolerance and prevents inflammatory reactions. Methods of genetically modifying the adult islet beta cells of the present invention are described hereinabove.

Since the islet cells of the present invention express insulin, they may be used for treating a disease which is associated with insulin deficiency such as diabetes.

It will be appreciated that cells committed to the pancreatic endocrine lineage that do not yet express insulin levels similar to those in naturally occurring islets may also be used for implantation (immature islet cells), provided they co-express Pdx1, Nkx6.1 and MAF-A. These cells might be stimulated to maturate, i.e to express high levels of insulin, when they are in the correct in vivo environment.

Thus, according to another aspect of the present invention there is provided a method of treating diabetes in a subject, the method comprising transplanting a therapeutically effective amount of the islet cells of the present invention into the subject, thereby treating diabetes.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein, "transplanting" refers to providing the islet cells of the present invention, using any suitable route. Typically, beta cell therapy is effected by injection using a catheter into the portal vein of the liver, although other methods of administration are envisaged (e.g. subcutaneous or intraperitoneal or in fat tissues).

The islet cells of the present invention can be derived from autologous sources, semi-autologous sources or from allogeneic sources. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang™ and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

If appropriate, the patient can be further treated with pharmaceutical agents or bioactives that facilitate the survival and function of the transplanted cells. These agents may include, for example, insulin, members of the TGF-beta family, including Activin A, TGF-beta1, 2, and 3, bone morphogenic proteins (BMP-2, -3, -4, -5, -6, -7, -11, -12, and -13), fibroblast growth factors-1 and -2, platelet-derived growth factor-AA, and —BB, platelet rich plasma, insulin-like growth factors (IGF-I, II) growth differentiation factor (GDF-5, -6, -7, -8, -10, -11, -15), vascular endothelial cell-derived growth factor (VEGF), Hepatocyte growth factor (HGF), pleiotrophin, endothelin, Epidermal growth factor (EGF), beta-cellulin, among others. Other pharmaceutical compounds can include, for example, nicotinamide, glucagon like peptide-I (GLP-1) and II, GLP-1 and 2 mimetibody, Exendin-4, retinoic acid, parathyroid hormone.

Indolactam V, or PMA, or MAPK inhibitors, such as, for example, compounds disclosed in U.S. Published Application 2004/0209901 and U.S. Published Application 2004/0132729.

The cells of the present invention may be transplanted to a human subject per se, or in a pharmaceutical composition where it is mixed with suitable carriers or excipients.

As used herein a "pharmaceutical composition" refers to a preparation of one or more of the cell populations described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in context of the present invention include compositions wherein the active ingredients are contained in an amount effective to achieve the intended purpose. More specifically, a therapeutically effective amount means an amount of active ingredients (insulin producing cells) effective to prevent, alleviate or ameliorate symptoms of a disorder (e.g., Diabetes) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models (e.g. STZ diabetic mice) to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The present invention also contemplates incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. No. 5,770,417, U.S. Pat. No. 6,022,743, U.S. Pat. No. 5,567,612, U.S. Pat. No. 5,759,830, U.S. Pat. No. 6,626,950, U.S. Pat. No. 6,534,084, U.S. Pat. No. 6,306,424, U.S. Pat. No. 6,365,149, U.S. Pat. No. 6,599,323, U.S. Pat. No. 6,656,488, U.S. Published Application 2004/0062753 A1, U.S. Pat. No. 4,557,264 and U.S. Pat. No. 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-beta family, including TGF-beta1, 2, and 3, bone morphogenic proteins (BMP-2, -3, -4, -5, -6, -7, -11, -12, and -13), fibroblast growth factors-1 and -2, platelet-derived growth factor-AA, and —BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

A Procedure for hES Cells Differentiation into Definitive Endoderm: Treatment with Activin a for Five Days Results in 75% Cells with Markers of the Definitive Endoderm Materials and Methods Growth of Human ES Cells:

Gamma-irradiated human foreskin (or cord blood) fibroblasts (HEF, 2-3×10$^5$ cells per well) were seeded on wells of costar 6×well tissue culture plate (Corning) coated with 0.1% porcine gelatin (Cell culture tested). Gelatin was dissolved in water at the concentration of 0.1 g per 100 ml double distilled water, and autoclaved. Fibroblasts were left 2 hours to overnight in an incubator at 37° C. in DMEM/F12, 10% fetal calf serum (FCS, InVitrogen), Glutamine 2 mM and Penicillin streptomycin (PS) (Biological Industries Bet Ha Emek).

Human ES cells after freezing or freshly dissociated with Collagenase IV (Worthington or InVitrogen) were seeded on HEFs at the concentration of about 450-500 ES cell clusters per well. The hES cells were cultured in growth medium (DMEM/F12 (Biological Laboratories Bet Ha Emek, Israel); 20% Knockout serum replacement (KOSR, Invitrogen); glutamine 2 mM (glut, Biological industries Bet ha Emek); β-mercaptoethanol (βMEtOH, Invitrogen) 100 μM; non essential amino acids 1× (NEEA, Invitrogen); Na Pyruvate (1 mM (NaPyr, Invitrogen) and 8 ng/ml of recombinant hbFGF (Preprotech). This medium was changed every day and did not contain antibiotics. Cells were left to grow for three to five days. Each colony grew to a diameter of 600-900 μm, containing an average of 3,300 undifferentiated hES cells (total around 2×10$^8$ cells).

For passaging the ES cells, the medium was removed before addition of 0.8 ml per well of collagenase IV, 1.2 mg/ml in DMEM/F12 with glutamine 2 mM. Cells were left with collagenase for 25 to 40 minutes, causing detachment of hESC clusters while not affecting HEF. The cell clusters were washed twice from collagenase by centrifugation at 900 rpm 5-6 min. The pellet was resuspended in 300 μl medium and if necessary (diameter bigger than 1 mm) the clusters'size was reduced to about 3-400 μm by up- and down pipetting with a 200 μl automatic pipette set at 1504 Treatment with collagenase was not performed for more than 3 plates at the same time.

Differentiation to Definitive Endoderm:

Step IA:

On day one, three wells of human ES cell colonies (grown on Corning 6×well plate for 4 days) detached by collagenase were collected into a 15 ml tube, and colonies washed twice by low speed centrifugation in differentiation medium A (DMEM/F12, 2% KOSR, 2 mM glutmine, 1×NEAA, 100 μM βMEtOH, 1 mM NaPyruvate and penicillin and streptomycin (PS)).

After all the hES clusters had been collected and washed, the clusters were suspended in 1.5 ml/well of differentiation medium A1, (i.e. differentiation medium A including 100 ng/ml recombinant human Activin A (Preprotech) and 25 ng/ml recombinant Wnt 3 (R&D), 2% knock-out serum replacement and 2 mg/ml bovine serum albumin (BSA, cell culture tested SIGMA)). 450-500 colonies/well were seeded in Costar 6×well plates which had been coated with 0.1% porcine gelatin (Sigma) 1 day before. Alternatively, about 3000 colonies were seeded on 10 cm diameter plates. Plates were left in the incubator (37° C., 5% $CO_2$) for 2 days without medium change.

Step IB:

On day 3, the medium was changed to differentiation medium A2 (DMEM/F12, 2% KOSR, 2 mM glut, 1×NEAA, 100 µM βMEtOH, 1 mM NaPyr and 2% Fetal Calf Serum (FCS)) containing 100 ng/ml Activin A and 2 mg/ml BSA. At this stage, clusters still floated and many single cells were visible. The plates were tilted so that clusters fell to the bottom edge of the well and the old medium was removed leaving clusters in 300 µl medium that is completed with 1.2 ml of medium A2. The collected culture medium that contained a few clusters was centrifuged at 900 rpm for 5 minutes. The pellet was re-suspended in 1.5 ml medium A2 and added to one of the wells. On day 4, most clusters adhered to the plate and the culture medium was changed similarly as on day 3, to differentiation medium A3 (DMEM/F12, 2 mM glutamine, 1×NEAA, 100 µM βMEtOH, 1 mM NaPyr but with 0.2% FCS) that contained 100 ng/ml Activin A and 2 mg/ml BSA. Cells were left in the medium A3 for 2 days.

Analysis by Indirect Immunofluorescence of the Expression of Markers Specific of the Definitive Endoderm:

Cells were fixed (4% paraformaldehyde in $Ca^{2+}$ and $Mg^{2+}$ free PBS for 20 minutes), washed ×3 with PBS and blocked with 10% horse serum in PBS. The reaction with the primary antibody (Ab) was performed in 10% horse serum with or without 1% BSA. Secondary antibodies (Either donkey anti mouse; donkey anti rabbit; donkey or rabbit anti-goat that are conjugated with fluorescent tags, Alexa 488 or Alexa 566 (Molecular Probes/Invitrogen) or with Cy3/donkey anti rabbit DyLight 488 (Jackson laboratories). Pictures were taken with a CCD camera and processed with an imaging program. Mouse monoclonal anti Sox17 Ab (R&D) 10 µg/ml was used with 0.1% Triton X100. Rabbit polyclonal anti FoxA2 (ab40874) (Abcam) was used at the dilution of 1/1000 with 0.1% Triton X100.

Results

Using the above protocol, it was found that at the end of 5 days of Activin A treatment, about 75% of the cells express Sox17 and/or FoxA2 (FIGS. 1A-F), indicating that cells were at the definitive endoderm stage. At low magnification, staining with FoxA2 (FIG. 1A) or Sox17 (FIG. 1D) shows that large areas are positive, whereas higher magnification show nuclear staining (FIG. 1B, E). It was calculated that about 75% of the nuclei express FoxA2 and/or Sox17. RNA extraction followed by RT-PCR with specific primers confirmed a strong expression of these markers. Immunostaining with anti-Oct4 antibodies indicated that only 5% of the cells were anti Oct4 positive at this time (not shown). At the end of the 5 day-treatment with Activin A, one can see about 200 adherent clusters per well of 6-well plates, (out of the initial 300-500 ES cell colonies seeded), indicating a good yield of definitive endoderm clusters.

Example 2

Treatment of Cells Derived from Step IA and IB with FGF10, Forskolin, and Retinoic Acid Results in High Percentage of Pdx1 Positive Cells Materials and Methods Differentiation of Definitive Endoderm Clusters to Pdx1 Positive Cells:

Step IIA.

On day 6, cells were washed with DMEM/F12, 2 mM glutamine, 1×PS, and medium changed to differentiation medium B1 (DMEM/F12, 2 mM glutamax (Invitrogen), 2 mg/ml BSA, 1% B27 supplement (In Vitrogen) 50 ng/ml human recombinant FGF10 (Preprotech), and 10 µM Forskolin (F-6886 from *coleus forskohlii* (SIGMA)). The cells were left two days in the same medium.

Step IIB.

On day 8, the medium was changed to differentiation medium B2 i.e. medium B1 with addition of 2 µM fresh *ATRA* (All trans retinoic acid) for five days. Medium was changed every two days.

Step III.

On day 13, medium was changed to DMEM/F12, Glutamine 2 mM, PS, 1×ITS supplement (Invitrogen), 2 mg/ml BSA, 5 µg/ml bovine fibronectin (Biological Industries Bet Ha'emek,), Nicotinamide 10 mM (SIGMA) and exendin-4, 5-50 ng/ml. Medium was changed every two days. Cells positive for C-peptide staining start to appear around day 19 of differentiation, but strong immunostaining for C-peptide appears at day 23 and positive islet like structures continue to form till day 50 and persist for at least 70 days. When the cells have differentiated more than 15-20 days, they can be further trypsinized and replated. On the second plating, islet-like structures appear 20-30 days after replating.

Analyses by Immunofluorescence:

Performed as in Example 1. Goat polyclonal anti-human Pdx1/IPF1 (R&D) antibody at 1:100 for 2 hrs, (blocking at 5% BSA in PBS with Triton 0.1%) was used. Mouse monoclonal Ab anti Nkx6.1 (Development Study Hybridoma Bank DSHB) were also used (data not shown).

Results

At day 14 of the differentiation protocol, i.e. two days after the end of the retinoic acid treatment, about 50% of the cultured cells express Pdx1. FIGS. 2A-E show that in some regions almost all the cells are Pdx1 positive. The lower overall percentage of Pdx1 positive cells relative to Sox17 expression is due to the fact that the differentiation occurs in cell clusters. FIGS. 2B-E show that Pdx1 staining co-localize with DAPI staining (2B) and show that Pdx1 staining is nuclear. FIGS. 2F-I shows that after 21 days of differentiation there is induction of insulin in domains of cells that are co-stained with Pdx1.

From day 25 of differentiation, the monolayer tears out and epithelial buds (i.e areas of high cell density) surge from the monolayer. FIGS. 3A-D show that, after 32 days, the epithelial buds are typically Pdx1 positive. When the culture was treated with Nicotinamide and exendin-4 (5 ng/ml) for the last 20 days, the monolayer and the buds were Pdx1 positive (FIGS. 3A-B). When the plate was treated only with Nicotinamide, the monolayer was less Pdx1 positive than when exendin-4 was used (FIGS. 3C-D). Counting the cells confirmed that Exendin-4 addition has a positive effect on the percentage of Pdx1 positive cells, at concentrations of 5-50 ng/ml (data not shown).

Figures 4A, 4B, 4C:
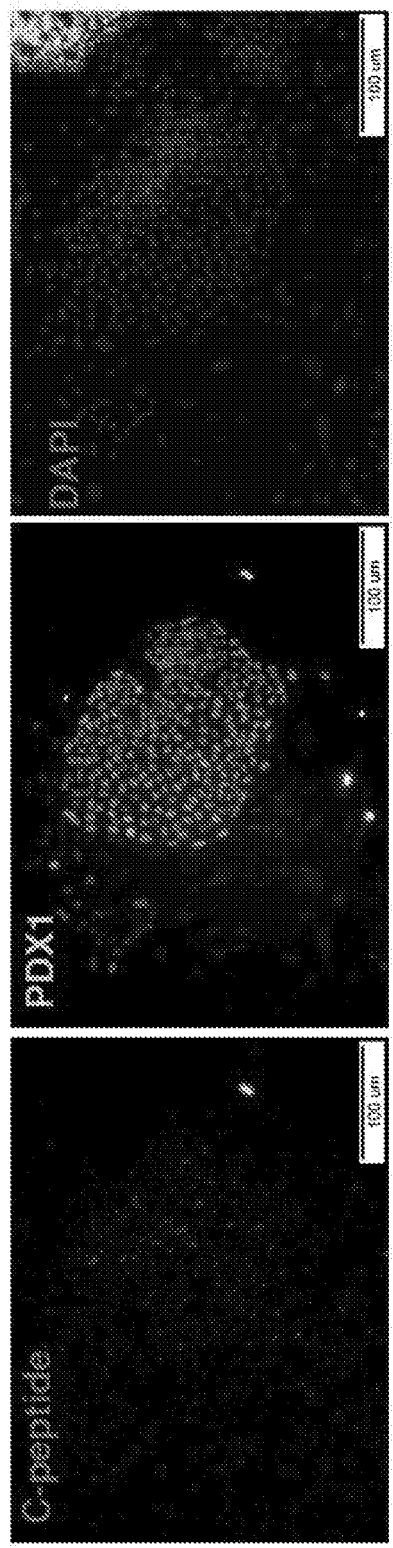
FIGS. 4A-C are photographs illustrating that differentiation also occurs when cells are trypsinized following activin A treatment. Cells dissociated by trypsin on day 7 and replated on new gelatin-coated plates for further culture are shown at day 29. Large islands of Pdx1 positive cells that are also C-peptide positive are seen.

A further increase in percentage of Pdx1 was achieved by trypsinizing the culture on day 7 and replating the dissociated cells on new gelatin-coated plates (FIGS. 4A-C). Islets with mostly Pdx1 positive cells were frequently observed under these conditions.

Example 3

Formation of Islets with Insulin- and Glucagon Producing Cells

Materials and Methods

Cultures obtained as in Examples 1 and 2 were further cultured in ITS medium (as detailed in step III of Example 2)

and were stained using polyclonal rabbit antibody to C-peptide (Acris) or monoclonal antibody (MAB 1975, Abcam) at dilution 1:200 overnight. To detect glucagon-produing cells, the cultures were also stained with goat polyclonal antibody against Glucagon (Santa Cruz N-17) at the concentration of 1:200 over night. The glucose transporter Glut2 was detected with mouse monoclonal Anti Glut-2 antibodies (R&D systems) used at the concentration of 1:200. Secondary antibodies were donkey anti-rabbit, donkey anti-goat or donkey anti-mouse conjugated with DyLight 549 or 488 (Jackson Laboratories) 1:200 for two hours.

Results

Specific C-peptide staining in the cell cytoplasm was clearly observed at day 37 of the differentiation process (FIGS. 5A-D). Such C-peptide staining can appear already from day 20-25. In the experiment depicted in FIGS. 5A-D, exendin-4 (50 ng/ml) was given from day 13 to day 29, the culture being then continued in ITS medium (Step III of Example 2). At day 37, many islet-like domains showed intense staining for C-peptide in the cytoplasm of cells, many of which were also Pdx1 positive (FIGS. 5A-D). Exendin-4 can also be administered continuously and even at lower concentrations (5 ng/ml). Under these conditions, the islet-like structures on day 37 appear more compact and better structured (FIGS. 6A-E). Double staining for insulin C-peptide and for glucagon, shows (FIGS. 6A-E) that about one third of the cells in such islets produce glucagon (alpha-cell phenotype) and two third produce insulin (beta cell phenotype). The differentiation process reproduces therefore the structure of natural pancreatic islets of Langerhans.

Figure 7G:
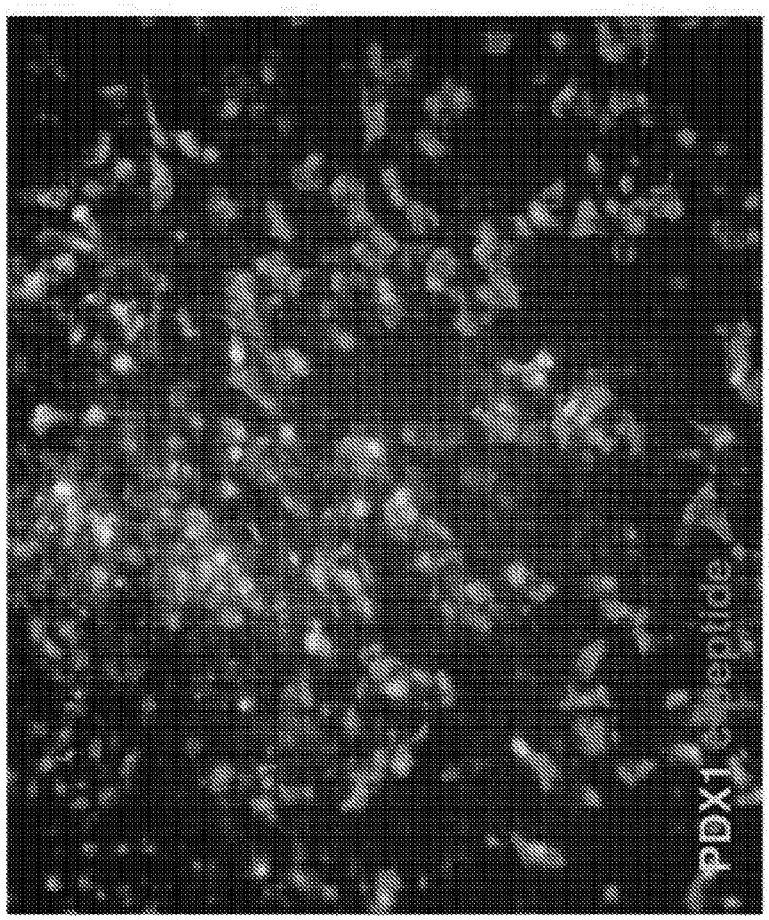
Figure 9B:
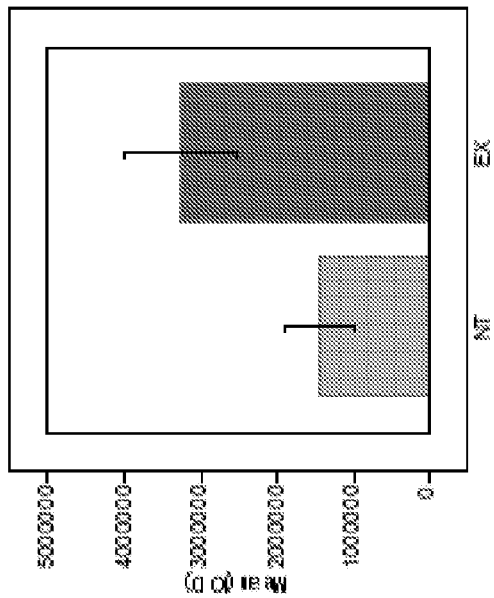
FIGS. 9A-B are graphs illustrating the effect of low concentration of exendin-4 on formation of C-peptide positive cells. The graphs show that addition of exendin-4 (5 ng/ml) from day 13 to day 60 is sufficient to increase the total number of C-peptide positive cells (Integrated optical density, IOD.
Figure 9A:
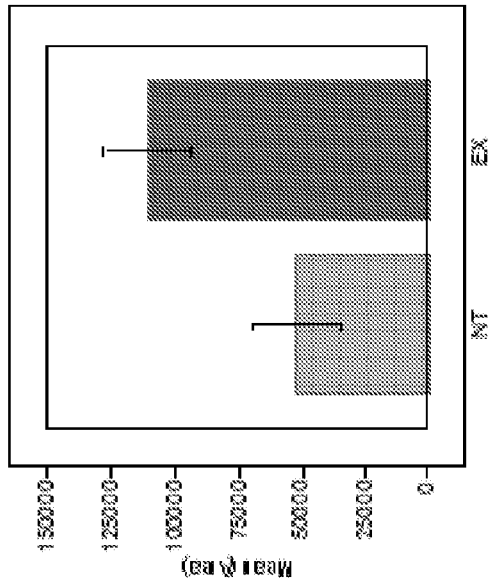

Islet-like domains of C-peptide positive cells continue developing at days 56-60 of differentiation (FIGS. 7 and 8). The C-peptide positive cells were positive for the glucose transporter transmembrane protein Glut-2, one of the proteins essential for the glucose-dependent insulin secretion (FIG. 7D). Glut-2 is a membranal protein and larger magnifications shows Glut-2 staining in the periphery of the cell (FIG. 7F). On day 56 of differentiation cells were co-stained with both C-peptide and Pdx1 (FIG. 7G)

At day 60, the C-peptide positive islet-like structures became more condensed. This is particularly clear with exendin-4 at 50 ng/ml (FIGS. 8A-F). Counting the number of C-peptide/glucagon positive areas indicated that there were 3 time more such areas in cultures with 50 ng/ml relatively to samples with 5 ng/ml exendin-4 (not shown). However, it was found that a low concentration of exendin-4 (5 ng/ml) was sufficient to increase the total amount of cells that were positive for C-peptide after 60 days of differentiation (FIGS. 9A-B) in comparison with control conditions without any exendin-4.

Figure 10:
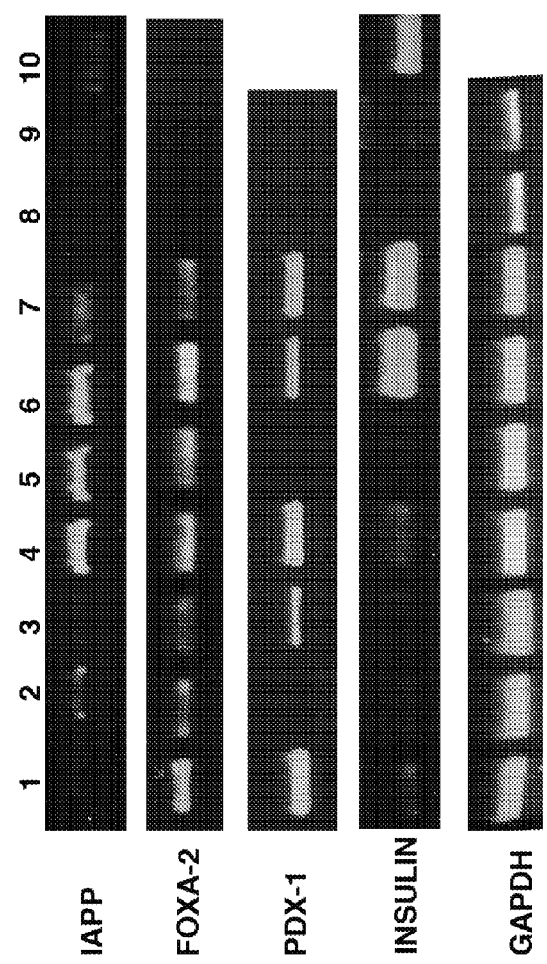
FIG. 10 is a photograph illustrating that insulin and Pdx1 mRNAs are increased during differentiation. Total RNA was isolated by RNAeasy kit (Qiagen) and 1 μg of RNA was reverse transcribed by Superscript II (Invitrogen) in 20 μl. 2 μl of the reaction product were taken for RT PCR with specific primers in 20 μl. Lane 1: Differentiation day 12; lanes 2 and 3: Differentiation day 25; lanes 4 and 5: Day 36 (without BSA in ITS medium); lanes 6 and 7: Day 36 (2 mg/ml BSA in ITS medium); lanes 8 and 9: Pluripotent ES cells; lane 10 human islet cDNA positive control (diluted 1:150 before reverse transcription).

When insulin mRNA concentrations were examined using semi-quantitative RT-PCR, it was found that insulin mRNA was high after 36 days of culture (i.e. during culture in ITS medium with nicotinamide and BSA), whereas FoxA2 and Pdx1 mRNA were present at earlier time points (FIG. 10).

Example 4

Effect of Exogenously Added Pdx1 mRNA in the Course of hES Cell Differentiation

Materials and Methods

The human Pdx1 cDNA was amplified by PCR from the original plasmid pcDNA3 Pdx1 using reverse and forward primers that contain respectively EcoRI and Msc1 sites. The PCR fragment was cloned in the plasmid PTMA-GFP from which the GFP sequence was excised using Msc1 and EcoR1. The 5' UTR of the cDNA comprises a consensus ribosomal entry site and in the 3' UTR the cDNA is followed by a polyT tail. The plasmid PTMA Pdx1 was linearized with SalI in 3' of the polyT tail and the mRNA was transcribed and 5' capped with the kit mMessage mMachine T7 (Applied biosystems/Ambion). After DNAse I treatment the RNA was recovered on RNA easy column (Invitrogen). RNA integrity was monitored by agarose gel electrophoresis and by RT-PCR using oligodT primers, and a primer covering the IRES region as well as Pdx1 specific primer. Human ES cell derivatives grown in 6-well plates, were RNA transfected after one day in medium B1 (stage IIA day 7)), on three consecutive days. Transfection was in one ml of antibiotic free differentiation medium B1 supplemented with 4 pig of in vitro transcribed and capped mRNA and 2 µl of Lipofectamine 2000 (InVitrogen). Analysis was performed 24 hour after the last transfection, on day 12 of the differentiation- and later on day 32 of the differentiation.

Results

As shown in FIGS. 11A-K, one day after the last transfection, without treatment with RA (day 12 of the differentiation), Pdx1 is largely expressed in most colonies (FIG. 11A-K). In contrast, when cells were not treated with RA and control-transfected, Pdx1 positive areas are scarce and very few cells are present in each area (FIGS. 12A-D).

When cells were analyzed twelve days after transfection, large domains of Pdx1 mRNA-transfected cells were shown as Pdx1 positive (FIGS. 11F-K). Within the Pdx-1 positive areas there were several domains of C-peptide positive cells (FIGS. 11H and K). In contrast, control-transfected cells, not treated with RA, do not show domains of Pdx1 positive cells that correspond to an area of C-peptide positive cells, and the Pdx1 signal is very weak in these non-transfected cells. FIGS. 11L-Q show that as expected Pdx1 staining is nuclear, C-peptide staining is cytoplasmatic and the costaining show that the majority of C-peptide cells are Pdx1 positive.

Figure 13A:
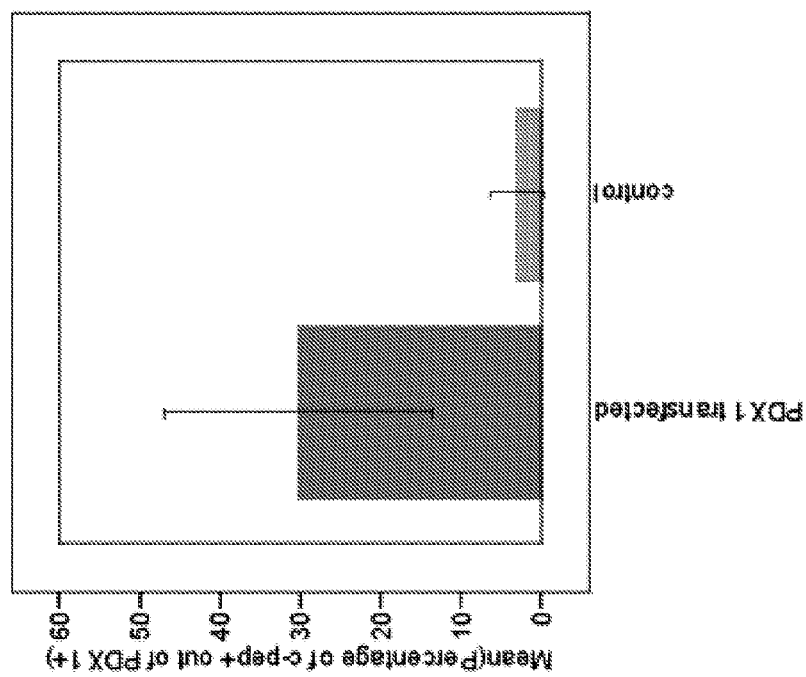
FIGS. 13A-B are graphs illustrating quantification of C-peptide positive cells with or without transfection with Pdx1 mRNA. The Figure presents quantitative analyses of data from the experiments shown in FIGS. 11 and 12.
Figure 13B:
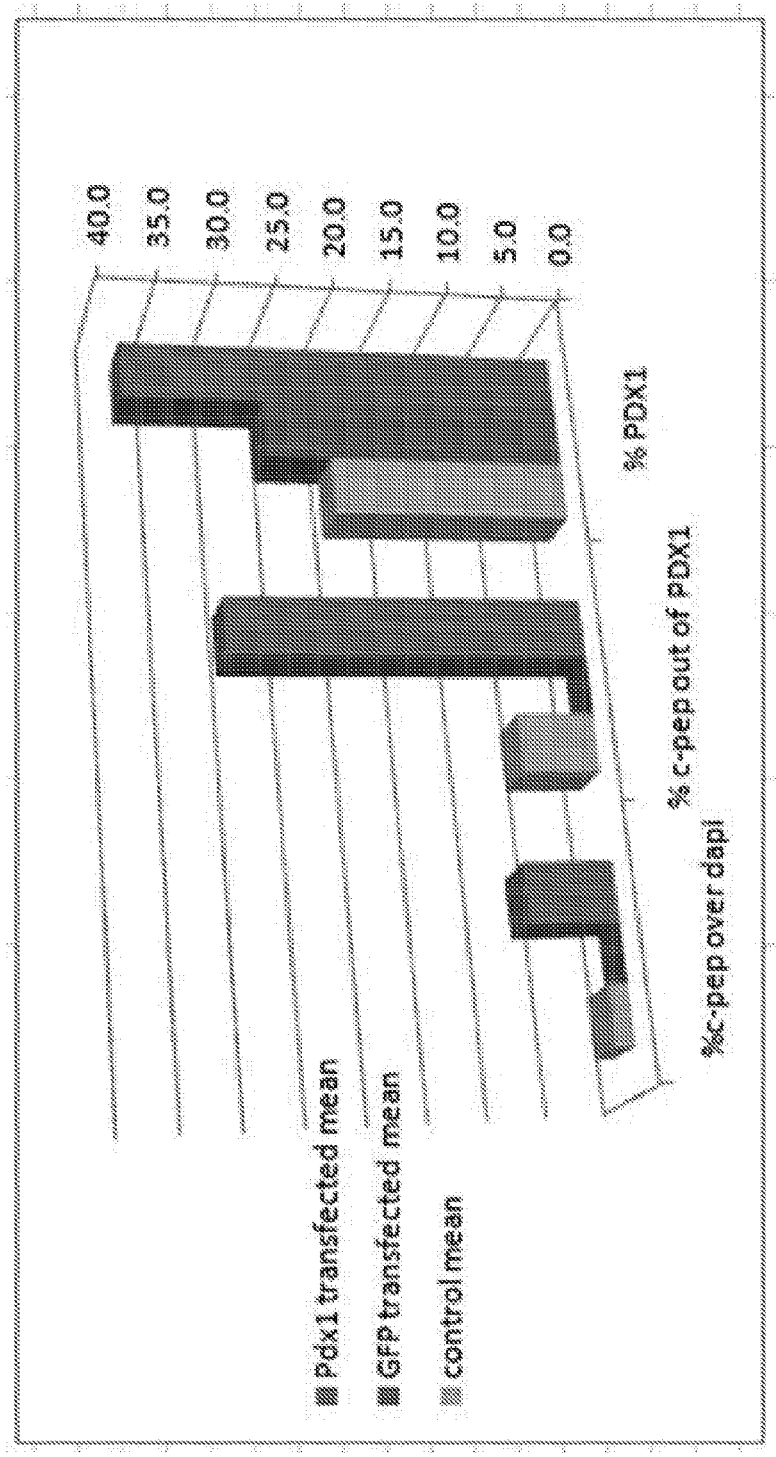

FIG. 13A demonstrates that exogeneously added Pdx1 mRNA markedly increases the percent of Pdx1 positive cells that become insulin producing cells as measured by C-peptide staining. FIG. 13B shows that Pdx1 mRNA transfection not only increases the ratio of C-peptide positive cells out of Pdx-1 positive cells but also the ratio C-peptide positive cells out of total cells (DAPI stained).

FIGS. 14A-H show that after Pdx1 mRNA transfection, two types of Pdx1 positive cells may be identified. Cells with large positive Pdx1 nuclei are very weakly stained by C-peptide antibody which probably represent progenitors (FIG. 14A-D). In other areas the Pdx1 staining is restricted small and compact nuclei that co-stained strongly for C-peptide. These cells probably represent more mature insulin producing cells. The Pdx1 protein that is present in the cells 21 days following transfection probably originate from activation of the endogenous gene.

This demonstrates that it is possible to influence over long term the destiny of embryonic stem cell derivatives by transfecting them with mRNA instead of using DNA plasmids.

Example 5

Differentiation of Human ES Cells and Isolation of EpCAM+ Population

Materials and Methods
Growth of Human ES Cells:
As described in Example 1.
Initial Differentiation of Human ES Cells:

The cells were initially differentiated towards definitive endoderm using a 3 step protocol as described in Example 1. The essential features of each of these steps is described in FIG. 15 (steps 1-3). Further differentiation was carried out as described in steps IIA, IIB and III of Example 2. The essential features of each of these steps is described in FIG. 15 (steps 4-6).

Figure 15:
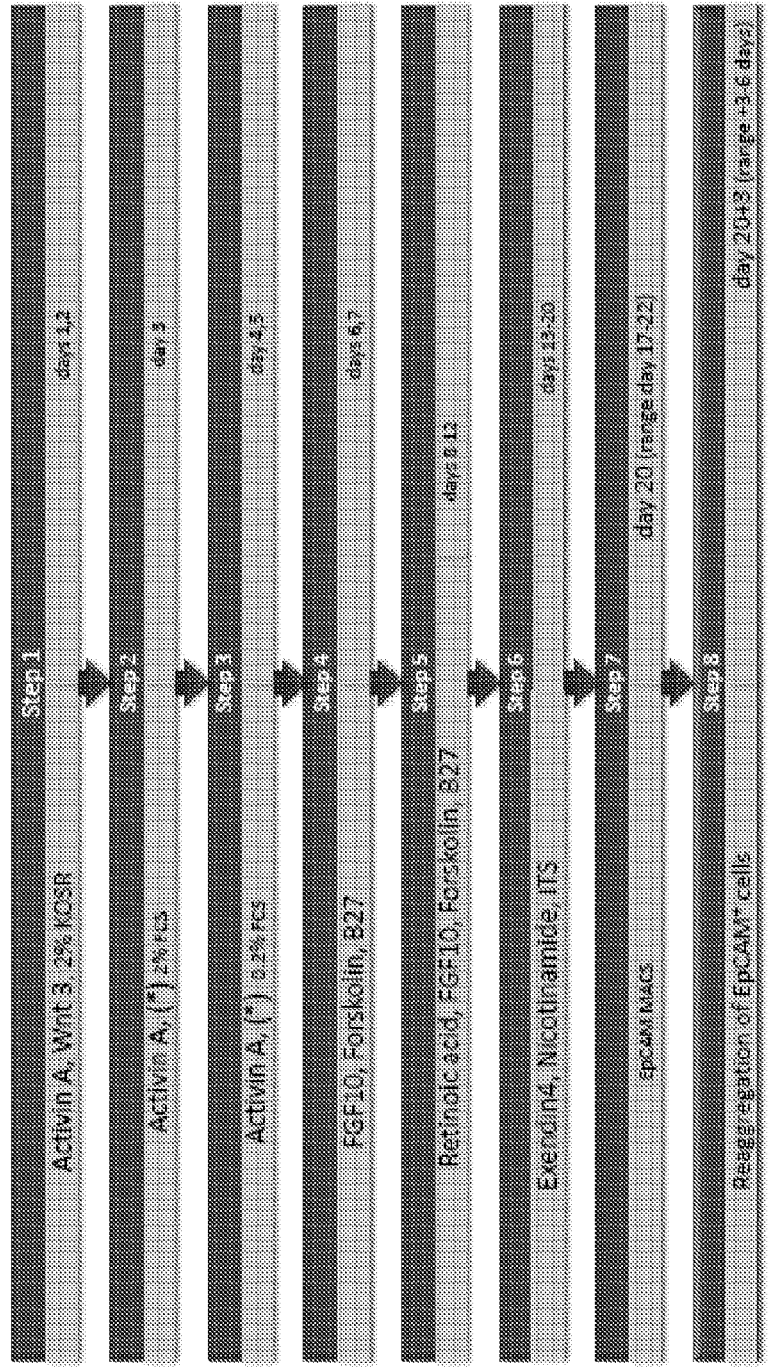
FIG. 15 describes an overall 8-step scheme for the differentiation of human ES cells into purified pancreatic islet-like clusters.

Further Differentiation of Human ES Cells—Steps 7 and 8 of FIG. 15:

Step 7:

On day 20, the medium used in step III of Example 2 was modified to adjust the glucose concentration to 5.5 mM (referred to herein as DM7). For isolation of EpCAM$^+$ cells by magnetic cell sorting (MACS technology, Miltenyi Biotec), a 10 cm-diameter plate was washed with PBS$^{-/-}$ (no Ca$^{++}$, no Mg$^{++}$). Cells were then dissociated by treatment with Accutase (Stempro, 2.5 ml/10 cm plate), for 10 minutes at 37° C., and pipetting up and down. The cells were collected in DM7 and an aliquot counted in a NucleoCounter (New Brunswick). Cells were centrifuged at 1,500 rpm (350×g) for 5 minutes and re-suspended in MACS buffer (PBS$^{-/-}$ with 0.5% BSA, 2 mM EDTA), using 0.3 ml for 50 million cells. Magnetic beads conjugated to anti-EpCAM antibodies (Miltenyi Biotec—CD326 pluripotent stem cells microbeads) were added (0.1 ml beads for 50 million cells). After 30 minutes at 4° C., the cells were washed once in 50 ml of MACS buffer, centrifuged, and finally re-suspended in 0.5 ml MACS buffer (for a maximum of 10$^8$ cells). The cell suspension was applied onto a MACS column (previously washed with MACS buffer), placed in the magnetic field of a MACS separator, and the flow through cell fraction was collected. After 4 washes of 3 ml, the column was removed from the separator and the retained cell fraction was collected. After centrifugation at 350×g for 5 minutes at 4° C., the pellets were re-suspended in 3 ml of DM7 or PBS In a modification of the above described procedure, the cells were collected in DM8, i.e. DM7 supplemented with 10 µM ROCK Inhibitor (Sigma #Y0503) and 1 µg/ml Laminin (human, of placental origin, Sigma #6274) following dissociation with Accutase. A treatment with DNase (Sigma #D4527), 20 µg/ml, was added to complete the cell dissociation prior to the EpCAM-MACS fractionation.

Step 8:

After isolating the EpCAM$^+$ cells (as in above), the cells were centrifuged at 350×g for 5 minutes and re-suspended at 10$^6$ cells per ml of DM7 or DM8 medium, and finally seeded in Ultra Low Binding plates (Corning, #cc-3471). The reseeded cultures were returned to the incubator (37° C., 5% CO$_2$) for 2-6 days. Microscopic observation allowed visualizing the re-aggregation of cells into clusters (FIG. 16). At the end of the re-aggregation period, the plates were subjected to a slow swirling motion and the cell aggregates were aspirated under a binocular microscope, and divided in aliquots for analysis.

Aliquots of the Presort culture and of EpCAM-MACS-separated fractions (from step 7), as well as of re-aggregated clusters (step 8) were analyzed. The number of cells was counted, using the Nucleocounter. After centrifugation at 350×g for 5 minutes, cell pellets were dissolved in M-PER (Mammalian protein extraction reagent, Pierce), typically using 0.1 ml M-PER for 2 million cells, and content of human insulin C-peptide was measured with an ELISA kit (Mercodia, Upsalh, Sweden, ultrasensitive c-peptide kit (minimal detection 5 pM) or Mercodia c-peptide ELISA (minimal detection 90 pM). Samples in M-PER were diluted 3 fold, or more in the kit buffer, and 20 µl of the ⅓ dilution were assayed. Results were expressed per mg total protein (as measured by Bradford assay) and per million cells (counted in a NucleoCounter). Other cell pellets were suspended in 0.7 ml buffer RLT (RNAeasy, Qiagen) per million cells, for RNA extraction. Human insulin mRNA was quantitated by RT-qPCR (Taq-Man, Applied Biosystems, Step One) using the TATA binding protein (TBP) gene as reference. In the same way, proteins and RNA were extracted from entire plates after scraping the cells with a rubber policeman.

Results

Figure 17:
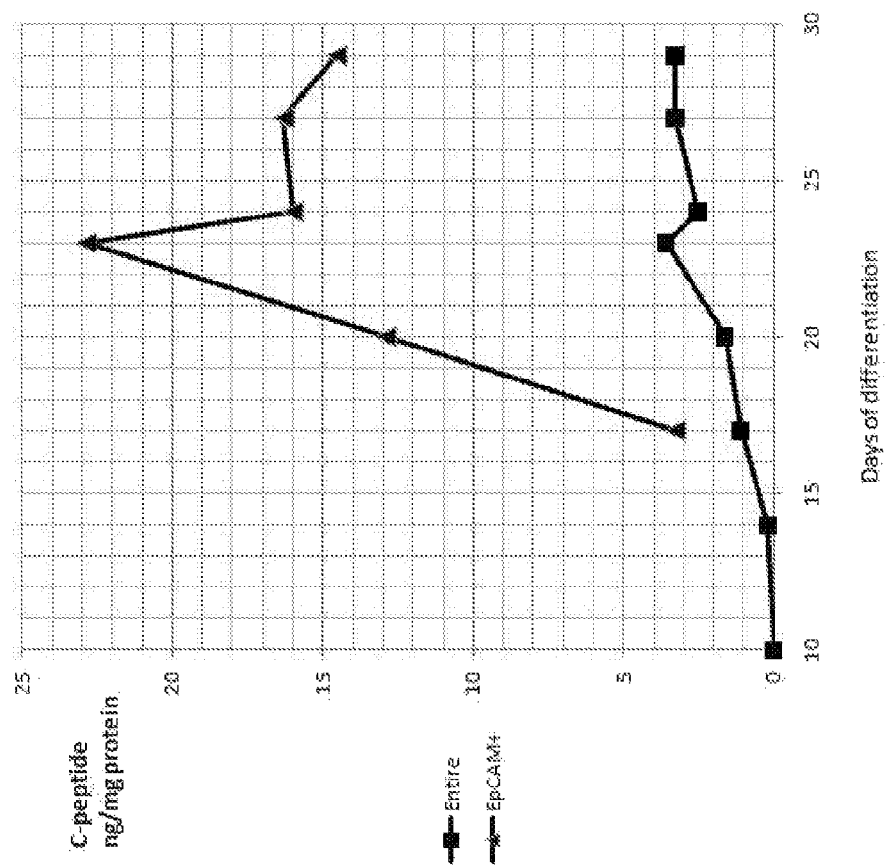
FIG. 17 is a graph illustrating the kinetics of C-peptide accumulation in the hES cell cultures (performed as described in FIG. 15). Black squares: the entire culture. Black triangles: in the EpCam$^+$ cell fraction after EpCam-MACS sorting.
Figure 18:
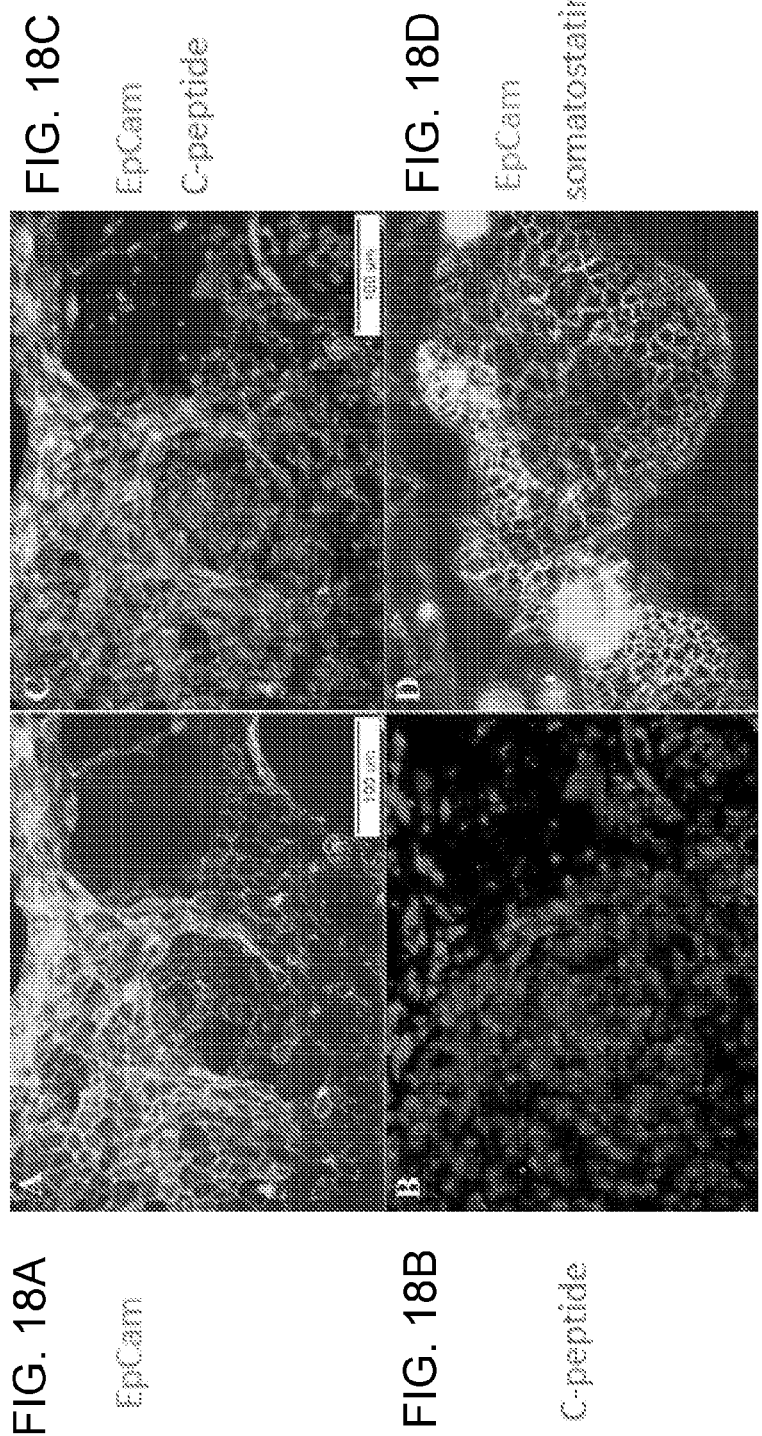
FIGS. 18A-D are photographs illustrating that most C-peptide expressing cells co-express EpCam. Cells at day 23 of differentiation were reacted with fluorescein-conjugated anti-EpCam Mc antibodies 326 (green) and phycoerythrin—(PE) conjugated anti C-peptide antibodies Mc AbCam 1975 (red). The co-expression of the two markers in the same cells is shown in FIG. 18C.

FIG. 17 shows that the insulin C-peptide content of the entire culture increased starting after day 14, reaching a plateau around day 23. The peak of the c-peptide content in EpCAM positive cells was around day 23 of the differentiation. At this time the cultures were immunostained with fluoroscein-conjugated anti-EpCAM antibodies (FIG. 18A) and phycoerythrin-conjugated anti C-peptide antibodies (FIG. 18B). Numerous EpCAM positive (EpCAM$^+$) structures were seen overlapping cell clusters expressing insulin C-peptide (FIGS. 18C, 3C). These EpCAM$^+$ cell clusters also contained glucagon positive cells (in red, FIG. 18D). Table 1, herein below shows the degree of enrichment of insulin C-peptide containing cells in the retained EpCAM$^+$ fraction, and a concomitant depletion in the flow-through (EpCAM$^-$) fraction.

TABLE 1

|   |   | Entire plate | MACS-Flow | Retain EpCAM+ |
|---|---|---|---|---|
| Expt 1 | Cell number | 100 × 10$^6$ | 42 × 10$^6$ | 2.2 × 10$^6$ |
| Day 23 | C-peptide ng/mg protein | 0.35 | 0.08 | 32.4 |
|   | C-peptide ng/10$^6$ cells | 0.01 | 0.0015 | 0.32 |
| Expt 2 | Cell number | 66 × 10$^6$ | 26.4 × 10$^6$ | 6.6 × 10$^6$ |
| Day 23 | C-peptide ng/mg protein | 3.59 | 0.20 | 22.9 |
|   | C-peptide ng/10$^6$ cells | 0.12 | 0.014 | 0.82 |

The EpCAM$^+$ fraction consistently contained about 70% of the total insulin C-peptide recovered (Table 1), which indicates that a majority of cells expressing insulin were EpCAM positive. The percentage of EpCAM$^+$ cells, as determined by FACS analysis in the entire dissociated culture, was in the range of 2-10% and the proportion of cells recovered in the fraction retained on EpCAM-MACS was in a similar range (Table 1). As analyzed by FACS analysis, the percent of EpCAM-positive cells in the flow through was usually 0.2-0.4% versus about 50% in the retained fraction.

The enrichment of insulin producing cells in the EpCAM$^+$ fraction was confirmed by measure of insulin mRNA content by qPCR. In Experiment 2 of Table 1, on day 23, the ratio of human insulin mRNA to the reference TBP mRNA was 0.59 in the entire culture versus 2.23 in the EpCAM$^+$ fraction. In contrast, in the EpCAM-minus fraction, the insulin to TBP ratio was 0.0127, which allows one to ascertain that over 99.4% of the cells expressing insulin mRNA were in the EpCAM$^+$ fraction.

After re-aggregation of the EpCAM$^+$ cells, the content of insulin C-peptide was higher than in the dissociated EpCAM$^+$ cells, as illustrated in Table 2, herein below.

TABLE 2

|  | Days of EpCAM sorting days of reaggregation | Duration of reaggregation | Addition during reaggregation | C-peptide ng/mg protein (fold) |
|---|---|---|---|---|
| Expt 1 | D17 (Presort) |  |  | 0.31 (1) |
|  | D17 (EpCAM+) |  |  | 1.07 (3.4) |
|  | D17 + 6 (reaggregated) | 6 days |  | 7.50 (24.2) |
|  | D23 (EpCAM+) |  |  | 7.50 (24.2) |
| Expt 2 | D20 (Presort) |  |  | 0.22 (1) |
|  | D20 (EpCAM+) |  |  | 1.93 (8.7) |
|  | D20 + 3 (reaggregated) | 3 days |  | 5.10 (23.2) |
|  | D23 (EpCAM+) |  |  | 2.00 (9.1) |
| Expt 3 | D22 (Presort) |  |  | 0.45 (1) |
|  | D22 (EpCAM+) |  |  | 1.29 (2.8) |
|  | D22 + 2 (reaggregated) | 2 days |  | 2.43 (5.4) |
|  | D22 + 2 (reaggregated) | 2 days | 1 mM EDTA | 3.46 (7.7) |
|  | D24 (EpCAM+) |  |  | 2.07 (4.6) |

Figures 16A, 16B:
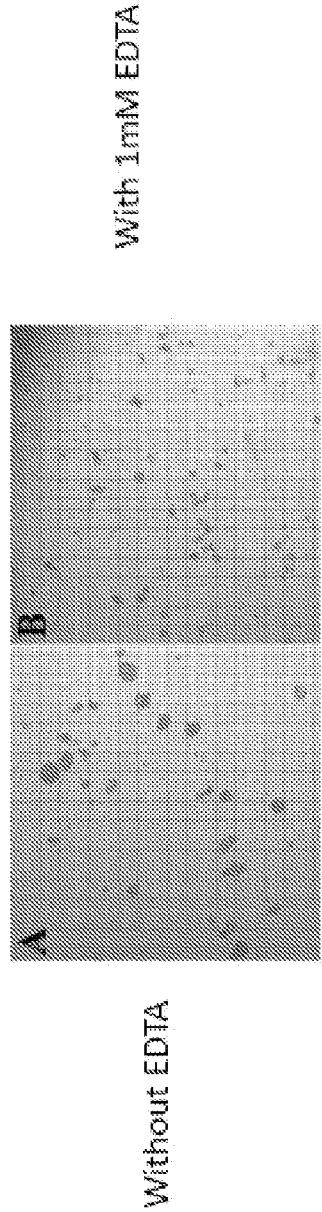
FIGS. 16A-C are photographs illustrating that the cells re-aggregating in suspension with EDTA remain alive. EpCam+ cells isolated at day 19 of differentiation were left in suspension for 4 days and photographed under the microscope. Cells left in suspension without addition of EDTA (A) form aggregates of bigger sizes than cells re-aggregated with EDTA (B). The live-dead reagents were applied to the purified aggregates at day 19+4 with EDTA 0.5 mM (C). The aggregates are formed of live cells that stain green.
Figure 16C:
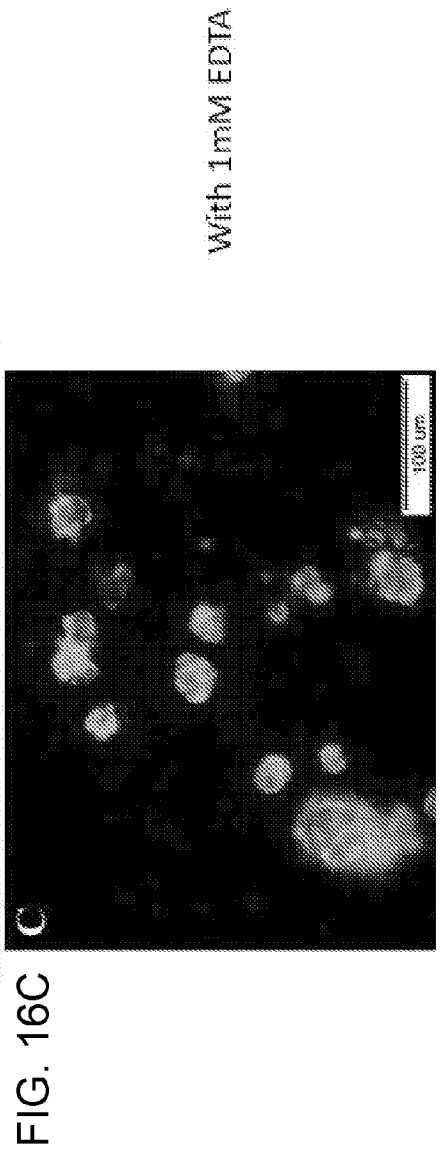

This is most likely due to a preferential re-aggregation of the insulin-producing cells. After EpCAM-MACS, the retained fraction (EpCAM+) is a heterogeneous population, since FACS analysis indicated that on the average only around 50% of the retained cells are highly EpCAM positive. After re-aggregation, about 20-30% of the cells were found in clusters of 20-100 microns, such as shown in FIG. 16A-C. The re-aggregation is, therefore, selective and the higher content of C-peptide in the re-aggregated clusters indicates that the insulin producing cells are enriched during the re-aggregation step.

Compared to the entire culture, the combination of the EpCAM-MACS and re-aggregation procedures resulted in an enrichment of over 20 fold in term of Insulin C-peptide content (ng/mg protein), when the procedure was done at days 17-20 (Table 2, Expt 1 and 2). The purification tended to decrease at later times (Table 2, Expt 3, day 24). Notably, when calcium-dependent cell-cell interactions were inhibited by addition of EDTA, there was a further increase in the C-peptide content (Table 2, Expt 3, and see Example 6).

Example 6

Purification of hES Cell-Derived EpCAM+ Cells Expressing Human Insulin mRNA and C-Peptide by Selective Reaggregation The purification of insulin producing cells produced by the combination of EpCAM-MACS sorting and re-aggregation of the EpCAM+ cell fraction was further evaluated by quantitative measure of insulin mRNA.

Materials and Methods

Differentiation of hES cells towards a pancreatic lineage: The hES cell cultures were differentiated as detailed in Example 5 and FIG. 15, steps 1-8, and RNA extracted at different steps was subjected to RT-qPCR. Table 3, herein below shows the ratio of Insulin mRNA to the reference gene TBP (TATA-binding protein).

TABLE 3

|  | Days of EpCAM sorting + days of reaggregation | Addition during reaggregation | Insulin mRNA ratio to TBP | C-peptide ng/$10^6$ live cell |
|---|---|---|---|---|
| Expt 1 | D17 (Presort) |  | 0.064 | 0.010 |
|  | D17 (EpCAM+) |  | 0.279 | 0.033 |
|  | D17 + 2 (reaggregated) |  | 1.311 | 0.840 |
|  | D19 (EpCAM+) |  | 0.333 | 0.110 |
| Expt 2 | D20 (Presort) |  | 0.067 | 0.011 |
|  | D20 (EpCAM+) |  | 0.151 | 0.035 |
|  | D20 + 3 (reaggregated) |  | 0.167 | 0.090 |
|  | D20 + 3 (reaggregated) | 0.5 mM EDTA | 0.459 | 0.100 |
|  | D20 + 3 (reaggregated) | 1.0 mM EDTA | 1.177 | 0.200 |
|  | D23 (EpCAM+) |  | 0.121 | 0.050 |
| Expt 3 | D19 (Presort) |  | 0.410 | 0.062 |
|  | D19 (EpCAM+) |  | 2.400 | 0.287 |
|  | D19 + 4 (reaggregated) |  | 3.030 | 0.857 |
|  | D19 + 4 (reaggregated) | 1.0 mM EDTA | 9.960 | 1.255 |
|  | D23 (EpCAM+) |  | 2.040 | 0.266 |

The level of insulin mRNA was increased about 20 fold in the re-aggregated clusters as compared to the presorted cell population. The enrichment was increased when EDTA was added during the re-aggregation step. Table 3 also shows that EpCAM+ cells extracted from parallel cultures on the day coinciding with the end of the re-aggregation step had lower insulin mRNA than the re-aggregated clusters, indicating that the enrichment was not due to the longer time of culture.

The number of cells in the re-aggregated clusters was determined in a Nucleocounter after re-dissociation with Accutase (see Example 5). The C-peptide content per million live cells shows similar enrichment as the level of insulin mRNA (Table 3).

Example 7

Re-Aggregation of Single EpCAM Cells into Islet-Like Structures that Contain Beta, Alpha and Delta Cells Materials and Methods Human ES cells were subjected to the differentiation protocol as outlined in FIG. 15 (steps 1 to 7). Accordingly, at day 20 of differentiation, the culture was dissociated by Accutase treatment and EpCAM+ cells were purified by EpCAM-MACS (as in step 7 of FIG. 15). The suspension of single EpCAM+ cells was subjected to re-aggregation for 4 days (as in step 8 of Example 1). The re-aggregated clusters were fixed in PFA, washed, equilibrated with 30% sucrose and finally embedded in optical cutting temperature compound (OCT). Fluorescent immunostaining was performed on 12 mm thick frozen sections. The slices were stained for C-peptide, glucagon and somatostatin, as well as DAPI.

Results

Figure 19:
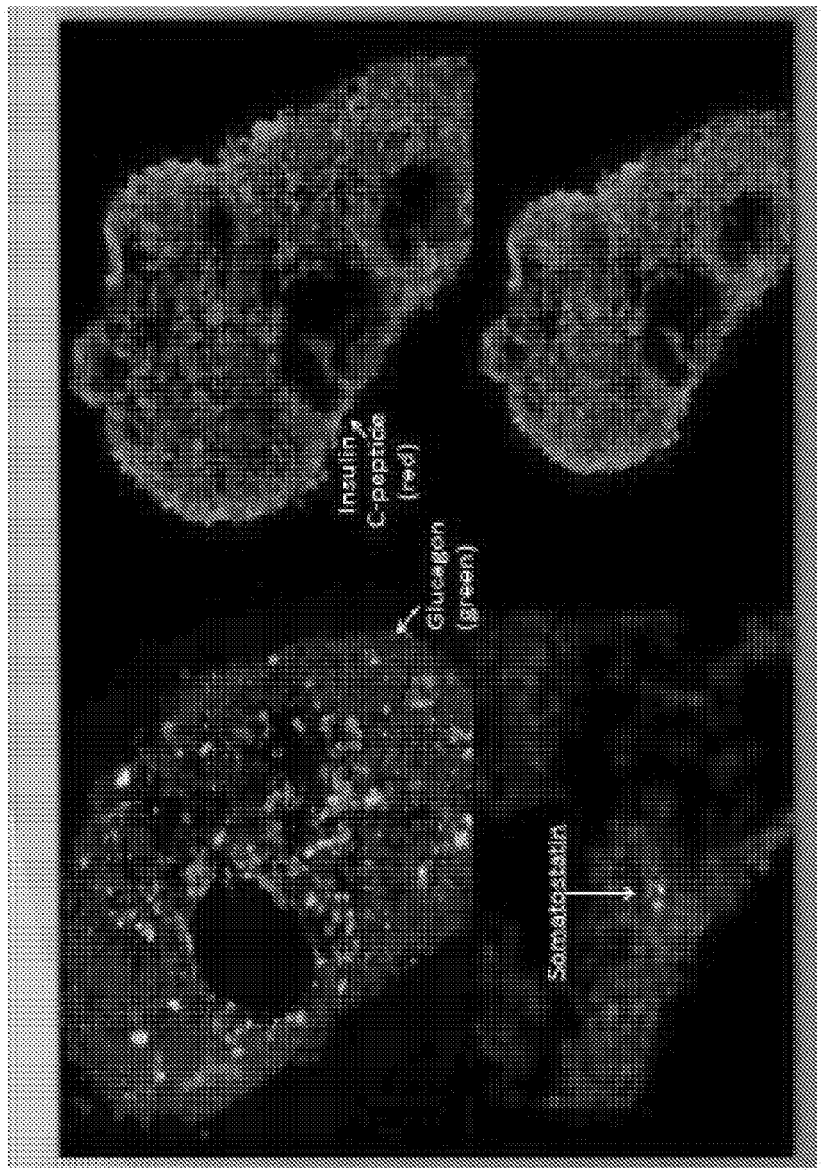
FIG. 19 is a photograph illustrating that most of the re-aggregated cells are c-peptide positive and some of the cells also express Glucagon. The EpCam positive cells isolated at day 20 of the differentiation procedure were cultured in suspension for 4 days, fixed with PFA 4%, equilibrated with 30% sucrose, and embedded in OCT. Frozen sections of 12 μm on glass slides were stained with the following antibodies. A: goat polyclonal anti-glucagon antibody (Santa Cruz) and donkey anti-goat Igg conjugated with FITC (Jackson); B: mouse monoclonal anti c-peptide Ab AbCAm 1975 conjugated with PE; C: rabbit anti-somatostatin antibody with donkey anti rabbit FITC; D is an overlay of anti c-peptide staining as in B and nuclear staining with DAPI.

FIG. 19 shows that the purified clusters had islet-like morphology and contained cells producing different islet-specific hormones. The majority of cells were stained for insulin C-peptide (FIGS. 19B, 19D), whereas a sizeable proportion of the cells were stained for glucagon (FIG. 19A) and a minority of cells were stained for somatostatin (FIG. 19C). Since it was shown that in the attached cultures on day 20 the EpCAM-stained regions (see FIG. 18) contain glucagon-stained cells, and that the dissociated EpCAM+ cells after EpCAM-MACS also contain dissociated cells stained for glucagon, it can be concluded that during re-aggregation, there is a spontaneous assembly of insulin producing beta cells with glucagon-producing alpha cells, as well as somatostatin-producing delta cells, to form islet-like structures.

Selective re-aggregation in the presence of EDTA results in a higher enrichment in the insulin mRNA and C-peptide content (see Example 6). After embedding, slicing and staining, the islet-like structures obtained in the presence of 1 mM EDTA (FIG. 20B) are smaller than in the absence of EDTA (FIG. 20A), the size range being 50-100 microns (FIG. 20B). In the absence of EDTA, nuclear staining by DAPI shows that there are larger clusters of cells suggesting that cell aggregation is more heterogeneous than in the presence of EDTA (FIGS. 20A, 20B). Staining for EpCAM shows many EpCAM-negative cells in the clusters re-aggregated without EDTA (FIG. 20A,C) whereas there were few of such cells in clusters obtained with EDTA (FIG. 20B,D). Since cell-cell interactions mediated by EpCAM are calcium independent, it is likely that in the presence of EDTA the re-aggregation eliminates many EpCAM-negative cells resulting in a more selective re-aggregation and better purification of genuine islet cells.

Figure 21:
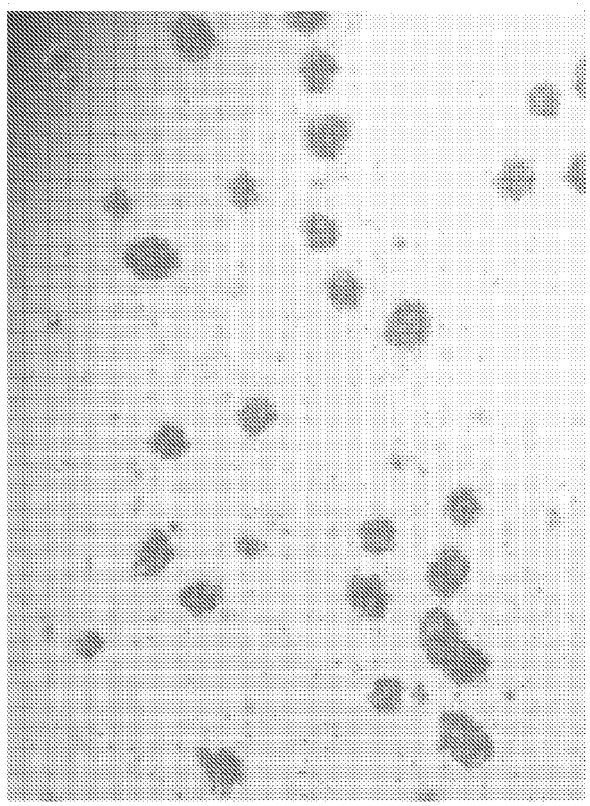
FIG. 21 is a photograph illustrating that cells re-aggregated in the presence of EDTA form small aggregates of homogeneous sizes (70-50 microns).

Dissociating the hES cell-derived cultures differentiated as in FIG. 15, followed by EpCAM-MACS sorting and re-aggregation of retained cells under conditions favoring calcium-independent cell-cell interaction is an effective way to obtain highly purified pancreatic islet-like structures, which under light microscopy appear as a homogeneous collection (FIG. 21).

Example 8

Differentiation with Serum Replacement (Instead of Serum) and Noggin (During Retinoic Acid Treatment) Followed by EpCam Purification and Re-Aggregation: Synergistic Increase in Insulin mRNA and C-Peptide Content The addition of fetal calf serum (FCS) in step 2 and 3 of the differentiation procedure (FIG. 15) is useful to facilitate attachment of the hES cell colonies to the gelatin-coated plates, but inhibits the efficacy of the Activin A treatment. Indeed, omission of FCS at these steps resulted in increased levels of insulin mRNA and C-peptide at the end of differentiation, but the viability of the cultures was reduced (not shown). Use of serum replacement, instead of FCS, allowed increasing cell viability and yields of insulin.

Materials and Methods

Figure 22:
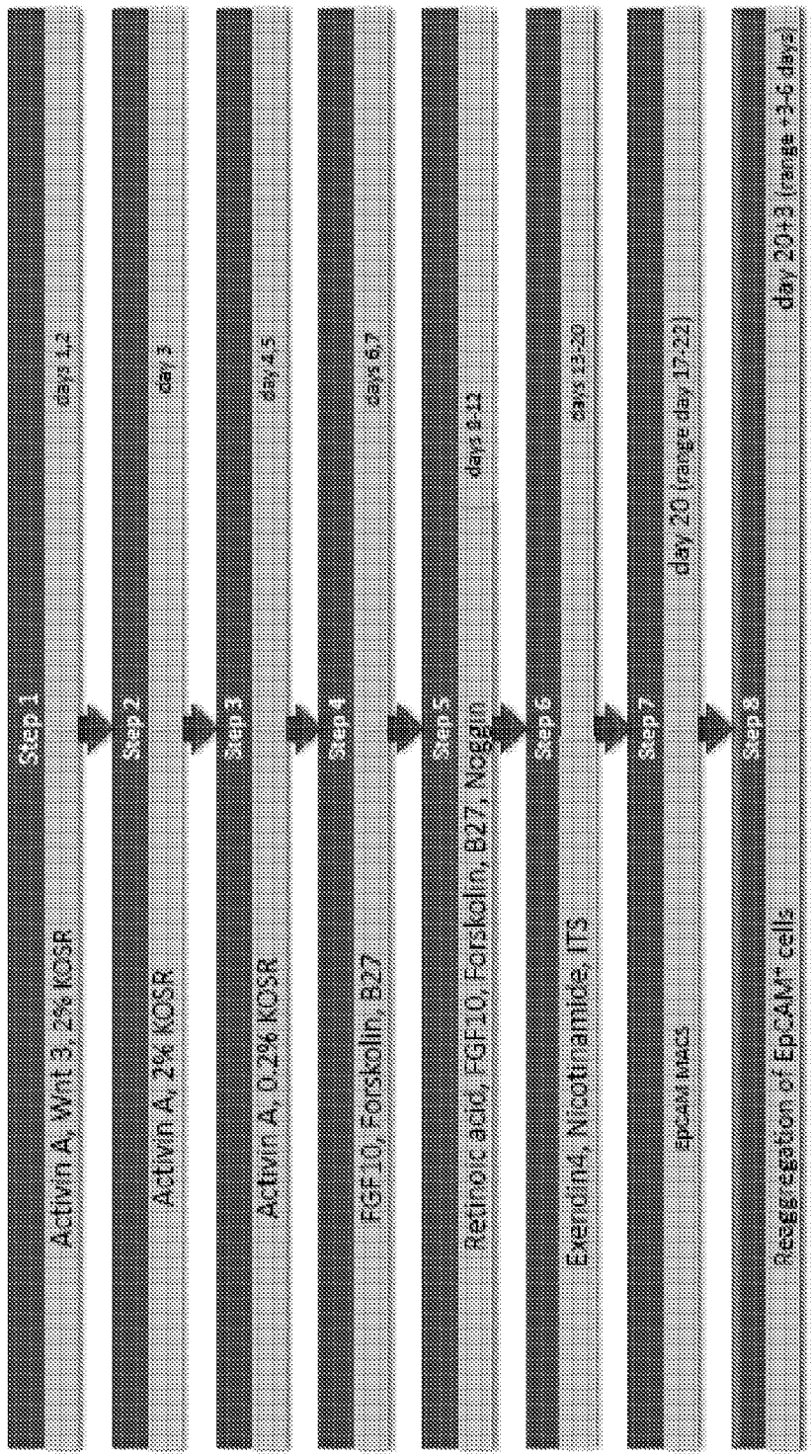
FIG. 22 describes an overall 8-step scheme for the differentiation of human ES cells into purified pancreatic islet-like clusters, according to embodiments of the present invention using serum replacement and noggin.

Human ES cells were differentiated according to the scheme illustrated in FIG. 22. Two modifications were made in the procedure detailed in Example 5. Thus, in step 2 and 3, the fetal calf serum was replaced by serum replacement (KOSR, Invitrogen), at the same concentrations (i.e. 2% in step 2, 0.2% in step 3). In addition, in step 5, Noggin (Preprotech) was added at 100 ng/ml. The EpCAM-MACS fractionation was performed as in Example 5.

The dissociated EpCAM+ cells were then reaggregated in the presence of EDTA (step 8, see Example 6). The aggregates were then collected by centrifugation at 50×g for 5 minutes, which allows separation from unreaggregated single cells.

Re-Aggretation of EpCam Positive Cells in Alginate Gel:

EpCam positive cells were allowed to re-aggregate inside the pores of an alginate gel (Algimatrix 3D Invitrogen). Porous Algimatrix gels are formed in the presence of 10% firming buffer. On day 19, EpCAM+ cells were seeded in medium DM8 with 5.5 mM glucose at $2 \times 10^6$ cells per well of 24 well plates in 0.5 ml medium, and centrifuged at 100×g for 4 minutes.

Testing for Glucose Responiveness:

On day 19+4, the medium was changed to RPMI 1640 Biological Industries, bet Ha Emek Israel) with penicillin streptomycin, glutamax, 0.2% BSA (Biological Industries, Bet HaEmek Israel) and 2.8 mM Glucose. Cells were incubated in this medium for one hour, after which the medium was removed and medium of same composition applied for 2 hours. After this time, triplicate wells were incubated in the same medium with 5.5 mM glucose, 27 mM glucose or 27 mM glucose with 30 mM KCl. The supernatant after 2 hours incubation was tested by ELISA for the insulin concentration released in the medium.

Results

A synergistic increase in the levels of C-peptide and insulin mRNA were observed when both modifications were applied, as compared to each change alone (Tables 4 and 5).

The combined use of KOSR at step 2-3 and of Noggin at step 5 resulted in the highest values for both C-peptide and insulin mRNA (Tables 4 and 5, respectively).

TABLE 4

| | Days of EpCAM sorting + days of reaggregation | Addition during reaggregation | Insulin C-peptide ng/mg protein | | | |
|---|---|---|---|---|---|---|
| | | | Standard | KOSR | Noggin | KOSR + Noggin |
| Expt 1 | D 19 (Presort) | | 1.1 | 5.0 | 2.9 | 9.0 |
| | D 19 (EpCAM+) | | 3.5 | 26.8 | 8.15 | 64.7 |
| | D 19 + 4 (reaggregated) | 1 mM EDTA | 18.9 | 153.3 | nd | 324.4 |
| | D 23 (EpCAM+) | | 1.5 | 85.4 | 17.5 | 169.3 |
| Expt 2 | D 20 (Presort) | | 1.0 | | | 17.5 |
| | D 20 (EpCAM+) | | 6.3 | | | 127.6 |
| | D 20 + 3 (reaggregated) | | nd | | | nd |
| | D 20 + 3 (reaggregated) | 0.5 mM EDTA | 9.5 | | | nd |
| | D 20 + 3 (reaggregated) | 0.75 mM EDTA | 18.1 | | | 338.2 |
| | D 20 + 3 (reaggregated) | 1.0 mM EDTA | 21.9 | | | 356.7 |
| | D 23 (EpCAM+) | | nd | | | 98.9 |

TABLE 5

| | Days of EpCAM sorting + days of reaggregation | Addition during reaggregation | Standard | KOSR | Noggin | KOSR + Noggin |
|---|---|---|---|---|---|---|
| Expt 1 | D 19 (Presort) | | 0.3 | 1.2 | 0.6 | 2.9 |
| | D 19 (EpCAM+) | | 0.7 | 2.7 | 0.7 | 14.5 |
| | D 19 + 4 (reaggregated) | 1 mM EDTA | 7.5 | 47.0 | nd | 67.4 |
| | D 23 (EpCAM+) | | 0.2 | 2.5 | 0.7 | 7.5 |
| Expt 2 | D 20 (Presort) | | 0.2 | | | 2.14 |
| | D 20 (EpCAM+) | | 0.8 | | | 17.8 |
| | D 20 + 3 (reaggregated) | | 1.2 | | | nd |
| | D 20 + 3 (reaggregated) | 0.5 mM EDTA | 3.2 | | | nd |
| | D 20 + 3 (reaggregated) | 0.75 mM EDTA | 4.5 | | | 51.9 |
| | D 20 + 3 (reaggregated) | 1.0 mM EDTA | 5.1 | | | 85.2 |
| | D 23 (EpCAM+) | | nd | | | nd |

Analysis by FACS of the percentage of EpCAM+ cells in the entire culture at day 20-23 indicated a reduction of around 2 fold when the modified protocol (with KOSR and Noggin) was used as compared to the standard protocol. The improved insulin yield is likely to be related to a better selection of the pancreatic endocrine cells at the EpCAM-MACS step, a selection which is completed by the selective re-aggregation, which eliminates many non-relevant cells.

Figure 23A:
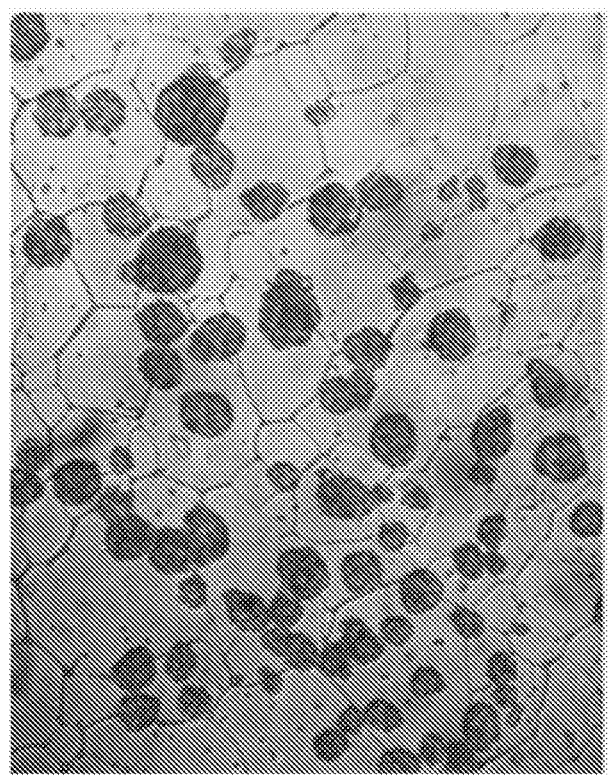
FIGS. 23A-B illustrate that aggregates of EpCam positive cells formed in porous Algimatrix (InVitrogen) respond to glucose stimulation by increase in insulin secretion. Cells differentiated with the as described in FIG. 22, for 19 days were dissociated. EpCam-positive cells, selected by MACS, were distributed to Algimatrix 24 well plate. Each well received $2 \times 10^6$ cells in DM8 and processed as described in the Examples section. A: Triplicate wells were exposed either to 2.8 mM glucose, 5.5 mM glucose, 27 mM glucose or 27 mM glucose with 30 mM KCl.
Figure 23B:
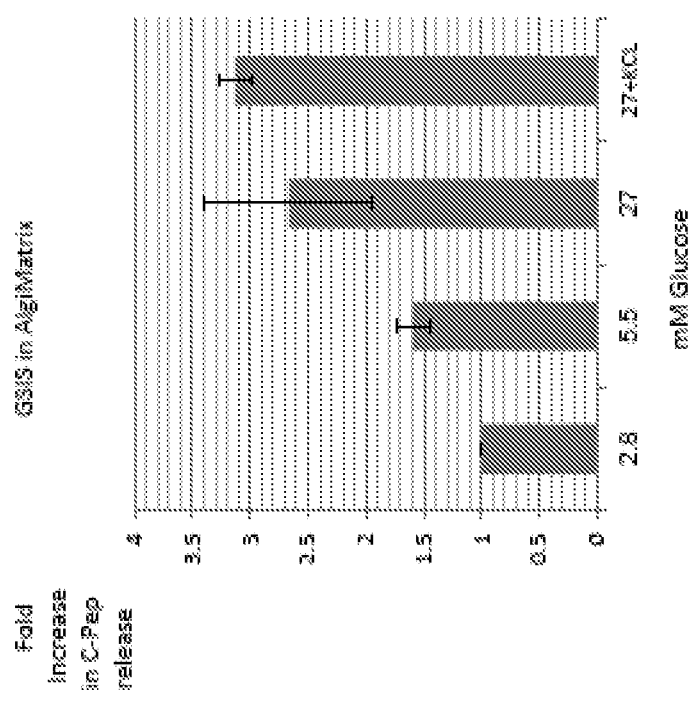

Functional beta cells secrete insulin in response to increase in blood glucose level. The present cells release insulin in response to increase in glucose concentration in the medium (FIG. 23). It can be seen in FIG. 23, the insulin release is increased 2.5 fold by increasing the glucose concentration from 2.8 to 27 mM while it is increased only by 50% by increasing glucose to 5.5 mM (FIG. 23A). The morphology of the aggregates isolated from the Algimatrix gel by treatment with EDTA is shown in FIG. 23B. Most of the aggregates are in the range of 50 to 100 mM diameter, while only very few of them are 200 mM or more diameter.

Of note, the content of insulin C-peptide (in ng/mg protein) in the alginate bioscaffold was the same as that observed in a parallel culture where the EpCAM+ cells were reaggregated in suspension in ultra-low binding plates.

Example 9

Evaluation of Therapeutic Effects of Human ES Cells in Streptozotocin (STZ)-Induced Diabetic Scid-bg Mice Materials and Methods Male SCID-bg mice, 7-8 weeks of age at study initiation were subjected to a single intraperitoneal (IP) injection of the β-cell toxin STZ at a dose level of 180 mg/kg and at a volume dosage of 6 ml/kg. Only animals that exhibited blood Glucose levels of >250 mg/Dl were subjected to implantation of $3 \times 10^6$ human ES cells (treated according to the differentiation protocol as outlined in FIG. 15). The single implantation was directed to under the left kidney capsule. Control mice group were sham injected.

Nonfasting blood glucose levels were determined once prior to STZ injection, once prior to implantation and 2× weekly thereafter until the end of the study. Measurements were carried out at about the same hour on each respective day using Glucometer. Blood samples were obtained via the tail vein.

Glucose tolerance test (GTT) was performed following food deprivation of approximately 16 hours, by IP injection or oral gavage (PO) administration of 50% Dextrose at a dose level of 2 g/kg. Blood Glucose levels were determined in all mice via the tail vein using Glucometer at the following time-points: Prior to Dextrose administration and 10, 30, 45, 60, 90 & 120 minutes following Dextrose administration.

Blood samples were collected following the GTT test (i.e. about 3 hours following Dextrose administration). Blood samples were obtained from the tail vein or by retro-orbital sinus bleeding. Whole Blood samples collected weekly for glucose level (a total of 2 samples) were confined to a volume not exceeding 20-25 µl/sample and for GTT & C-Peptide measurements confined to a volume not exceeding 10% of whole blood circulatory volume. The C-Peptide measurements following the IP GTT were collected 90 minutes post Dextrose administration. One week after the last IP GTT, the animals were euthanized and underwent nephrectomy.

The kidney was excised and was embedded in paraffin blocks or frozen for later histological analysis.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating human islet cells or human islet progenitor cells from human pluripotent stem cells and selecting for insulin producing cells, the method comprising:
   (a) culturing the human pluripotent stem cells for a period ranging from 5 to 8 days in a differentiation medium comprising glucose so as to differentiate the human pluripotent stem cells into endoderm cells expressing Sox17 and FoxA2;

(b) after obtaining said endoderm cells, culturing said endoderm cells for a period ranging from 2 to 10 days in a medium comprising forskolin, retinoic acid, glucose and at least one growth factor, the least one growth factor selected from the group consisting of FGF10, bFGF and FGF7 so as to generate PDX-1 positive cells;

(c) culturing said PDX-1 positive cells in a medium comprising glucose and at least one maturation factor selected from the group consisting of nicotinamide, GLP-1 and exendin 4, thereby generating islet cells or islet progenitor cells from pluripotent stem cells; wherein the generating of human islet cells or human islet progenitor cells is effected without the generating of embryoid bodies;

(d) dispersing said islet cells or islet progenitor cells to generate dispersed human islet cells or dispersed human islet progenitor cells;

(e) contacting said islet cells or islet progenitor cells with an agent that binds to EpCAM;

(f) selecting cells which bind to said agent;

thereby generating human islet cells or human islet progenitor cells that produce insulin; and (g) reaggregating said dispersed human islet cells or dispersed human islet progenitor cells that produce insulin.

2. The method of claim 1, wherein said differentiation medium comprises activin A.

3. The method of claim 2, wherein said differentiation medium comprises serum or serum replacement substitute.

4. The method of claim 2, wherein said differentiation medium is devoid of serum.

5. The method of claim 4, wherein said medium of step (b) further comprises noggin.

6. The method of claim 2, wherein said differentiation medium further comprises Wnt3.

7. The method of claim 1, wherein said culturing the pluripotent stem cells is effected by culturing collagenase-detached clusters of pluripotent stem cells on a gelatin coated surface.

8. The method of claim 1, wherein the human pluripotent stem cells comprise human induced pluripotent cells (iPP) cells.

9. The method of claim 1, wherein said re-aggregating is effected in a presence of an agent that chelates calcium selected from the group consisting of EDTA, EGTA, BAPTA, citrate, and phosphate.

10. The method of claim 1, further comprising seeding said dispersed islet cells on a scaffold.

11. The method of claim 1, wherein said re-aggregating is effected in a medium comprising glucose which is lower than that used in steps (a), (b) or (c).

12. The method of claim 1, wherein a glucose concentration of each of said media is between 5 mM-100 mM.

13. The method of claim 1, wherein the islet cells are glucose responsive, and synthesize insulin, glucagon or somatostatin.

14. The method of claim 1, wherein said endoderm cells do not express Oct4.

15. The method of claim 1, wherein step (a) or (b) is effected for about 5 days.

16. A population of islet cells or islet progenitor cells generated according to the method of claim 1.

17. A pharmaceutical composition comprising the population of cells of claim 16 as an active ingredient and a pharmaceutically acceptable carrier.

18. A method of treating diabetes in a subject in need thereof, the method comprising transplanting a therapeutically effective amount of the population of cells of claim 16 into the subject, thereby treating the diabetes.

19. The method of claim 1, wherein the culturing of said PDX-1 positive cells of step further comprises a maturation factor, wherein said maturation factor is nicotinamide, exendin 4, or a combination thereof.

* * * * *